295#

US011083777B2

(12) United States Patent
Wang et al.

(10) Patent No.: US 11,083,777 B2
(45) Date of Patent: Aug. 10, 2021

(54) HEMICHANNEL EXTRACELLULAR-DOMAIN SPECIFIC AGENTS FOR TREATING ISCHEMIA-REPERFUSION INJURY

(71) Applicant: The Feinstein Institutes for Medical Research, Manhasset, NY (US)

(72) Inventors: Haichao Wang, Edison, NJ (US); Wei Li, Plainview, NY (US); Kevin J. Tracey, Old Greenwich, CT (US); Ping Wang, Roslyn, NY (US)

(73) Assignee: The Feinstein Institutes for Medical Research, Manhasset, NY (US)

( * ) Notice: Subject to any disclaimer, the term of this patent is extended or adjusted under 35 U.S.C. 154(b) by 0 days.

(21) Appl. No.: 16/744,326

(22) Filed: Jan. 16, 2020

(65) Prior Publication Data

US 2020/0206310 A1 Jul. 2, 2020

Related U.S. Application Data

(62) Division of application No. 15/748,776, filed as application No. PCT/US2016/045284 on Aug. 3, 2016, now Pat. No. 10,548,949.

(60) Provisional application No. 62/201,759, filed on Aug. 6, 2015.

(51) Int. Cl.
| | |
|---|---|
| *A61K 38/17* | (2006.01) |
| *A61K 31/19* | (2006.01) |
| *A61K 31/22* | (2006.01) |
| *A61K 31/704* | (2006.01) |
| *C07K 16/18* | (2006.01) |
| *A61P 37/02* | (2006.01) |
| *A61K 38/08* | (2019.01) |
| *A61K 38/04* | (2006.01) |
| *C07K 14/00* | (2006.01) |
| *A61K 39/395* | (2006.01) |
| *A61P 31/02* | (2006.01) |

(52) U.S. Cl.
CPC .......... *A61K 38/177* (2013.01); *A61K 31/19* (2013.01); *A61K 31/22* (2013.01); *A61K 31/704* (2013.01); *A61K 39/395* (2013.01); *A61P 31/02* (2018.01); *C07K 14/00* (2013.01); *C07K 16/18* (2013.01); *A61P 37/02* (2018.01)

(58) Field of Classification Search
None
See application file for complete search history.

(56) References Cited

U.S. PATENT DOCUMENTS

2009/0142295 A1 6/2009 Becker
2014/0127190 A1 5/2014 Sand et al.

FOREIGN PATENT DOCUMENTS

| CN | 101573131 A | 11/2009 | |
|---|---|---|---|
| JP | 2003238441 A | 8/2003 | |
| WO | 2006134494 A2 | 12/2006 | |
| WO | WO 2013163423 | * 10/2013 | ............... C07K 7/08 |

OTHER PUBLICATIONS

Shintani-Ishida et al., Circ J 2009; 73: 1661-1668 (Year: 2009).*
Second Examiner's Report dated Apr. 17, 2020 from Canadian Patent Application No. 2,994,943.
PCT International Search Report and Written Opinion dated Nov. 30, 2016 in connection with PCT International Application No. PCT/US2016/045284, 10 pages.
Zhou et al., "Decreased Connexin 43 in Astrocytes Inhibits the Neuroinflammatory Reaction in an Acute Mouse Model of Neonatal Sepsis," Neuroscience Bulletin, Sep. 28, 2015 (Sep. 28, 2015), vol. 31, Issue 6, pp. 763-768.
Woehrle et al., "Hypertonic Stress Regulates T Cell Function via Pannexin-1 Hemichannels and P2X Receptors," Journal of Leukocyte Biology, Sep. 30, 2010 (Sep. 30, 2010), vol. 88, No. 6, p. 1181-1189.
Adamson et al., "The role of Pannexin1 in the Induction and Resolution of Inflammation," FEBS Letters, Mar. 15, 2014 (Mar. 15, 2014), vol. 588, pp. 1416-1422.
Yang et al., "Caspase-11 Requires the Pannexin-1 Channel and the Purinergic P2X7 Pore to Mediate Pyroptosis and Endotoxic Shock," Immunity, Nov. 10, 2015 (Nov. 10, 2015), vol. 43, Issue 5, pp. 923-932.
Bhattacharya et al., "Impact of Genetic Variation on Three Dimensional Structure and Function of Proteins," PLoS ONE 12(3): e0171355. https://doi.org/10.1371/journal.pone.0171355; Mar. 15, 2017, 22 pages. (Year: 2017).
Li et al., "Connexin 43 Hemichannel as a Novel Mediator of Sterile and Infectious Inflammatory Diseases," Scientific Reports, vol. 8, No. 166, Jan. 9, 2018, 16 pages. (Year: 2018).
Tokuriki et al., "Stability Effects of Mutations and Protein Evolvability," Current Opinion in Structural Biology 2009, vol. 19, Sep. 16, 2009, pp. 596-604. (Year: 2009).
Pirollo et al., "Targeted Delivery of Small Interfering RNA: Approaching Effective Cancer Therapies," Cancer Research 2008, vol. 68, No. 5, Mar. 1, 2008, pp. 1247-1250. (Year: 2008).
Winkler, "Oligonucleotide Conjugates for Therapeutic Applications," Ther. Deliv., vol. 4, No. 7, 2013, pp. 791-809. (Year: 2013).
Jafarlou et al., "An Overview of the History, Applications, Advantages, Disadvantages, and Prospects of Gene Therapy," Journal of Biological Regulators & Homeostatic Agents, vol. 30, No. 2, 2016, pp. 315-321. (Year: 2016).
Piche-Nicholas et al., "Changes in Complementarity-Determining Regions Significantly Alter IgG Binding to the Neonatal Fc Receptor (FcRn) and Pharmacokinetics," MABS, vol. 10, No. 1, 2018, pp. 81-94. (Year: 2018).
Japanese Office Action dated Jun. 30, 2020 from Japanese Patent Appln. No. 2018-506196, with English language translation.

(Continued)

*Primary Examiner* — Christina M Borgeest
(74) *Attorney, Agent, or Firm* — Amster, Rothstein & Ebenstein LLP

(57) ABSTRACT

Methods of treating sepsis or endotoxemia in a subject comprising administering to the subject an amount of an antagonist of a Panx1 hemichannel protein or an amount of an antagonist of a Cx43 hemichannel protein.

4 Claims, 10 Drawing Sheets

Specification includes a Sequence Listing.

(56) References Cited

OTHER PUBLICATIONS

O'Donnell III et al., "Gap Junction Protein Connexin43 Exacerbates Lung Vascular Permeability," PLoS One, vol. 9, No. 6, Jun. 2014, e100931, pp. 1-11.
Yoshida et al., "Inhibitory Effect of Glycyrrhizin on Lipopolysaccharide and D-Galactosamine-Induced Mouse Liver Injury," European Journal of Pharmacology, vol. 576, Aug. 2007, pp. 136-142.
Wang et al., "Glycyrrhizin Protects Against Porcine Endotoxemia Through Modulation of Systemic Inflammatory Response," Critical Care, vol. 17, No. 2, 2013, R44, pp. 1-13.
Japanese Allowance Decision for Patent dated Feb. 9, 2021 from Japanese Patent Application 2018-506196.
Chinese Office Action with Search Report dated Dec. 30, 2020 from Chinese Patent Application No. 201680046200.8.

\* cited by examiner

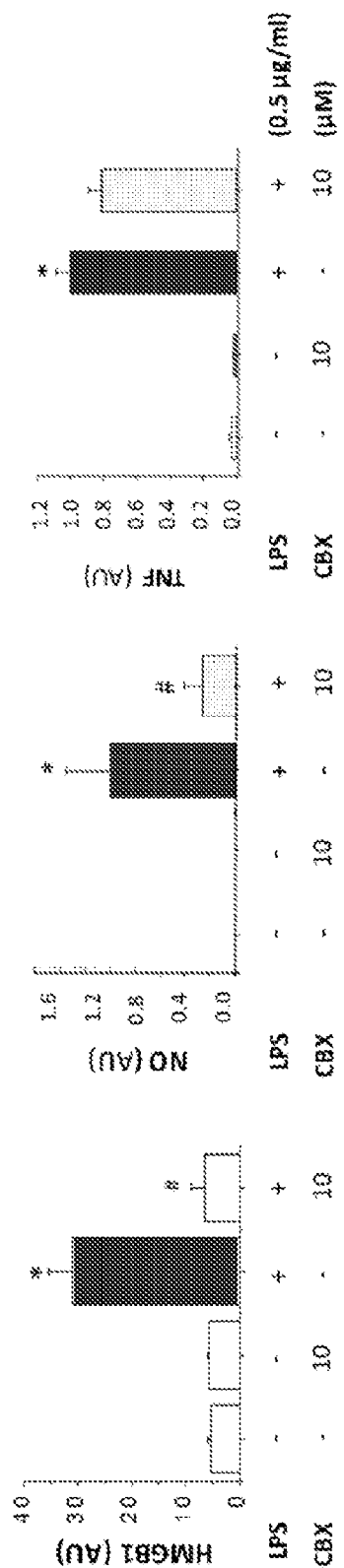

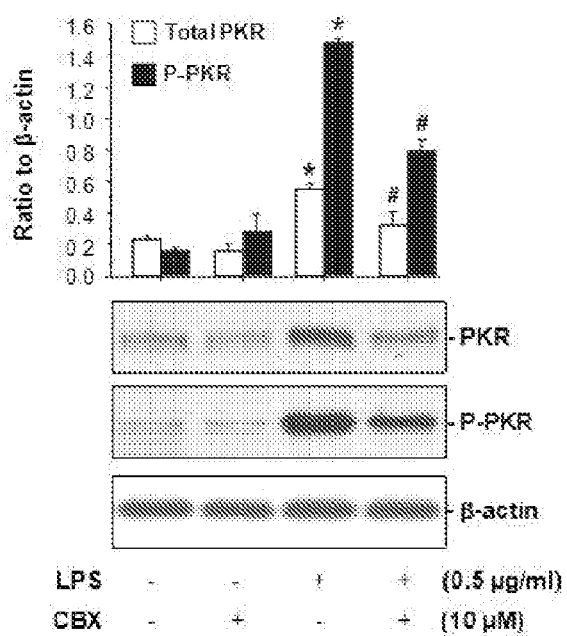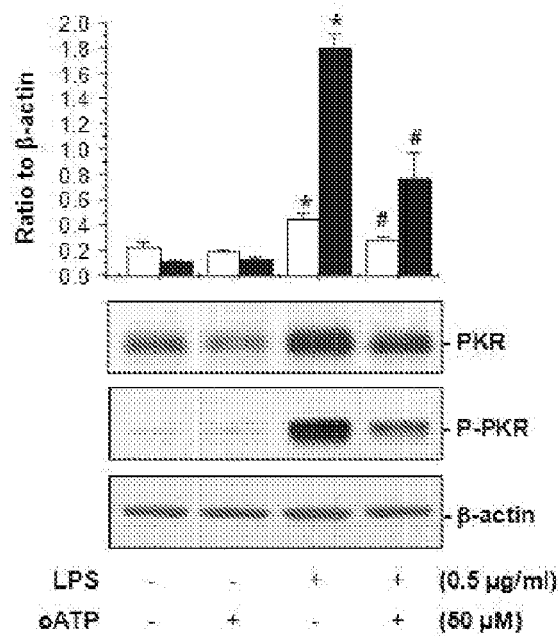
Fig 3A                    Fig 3B

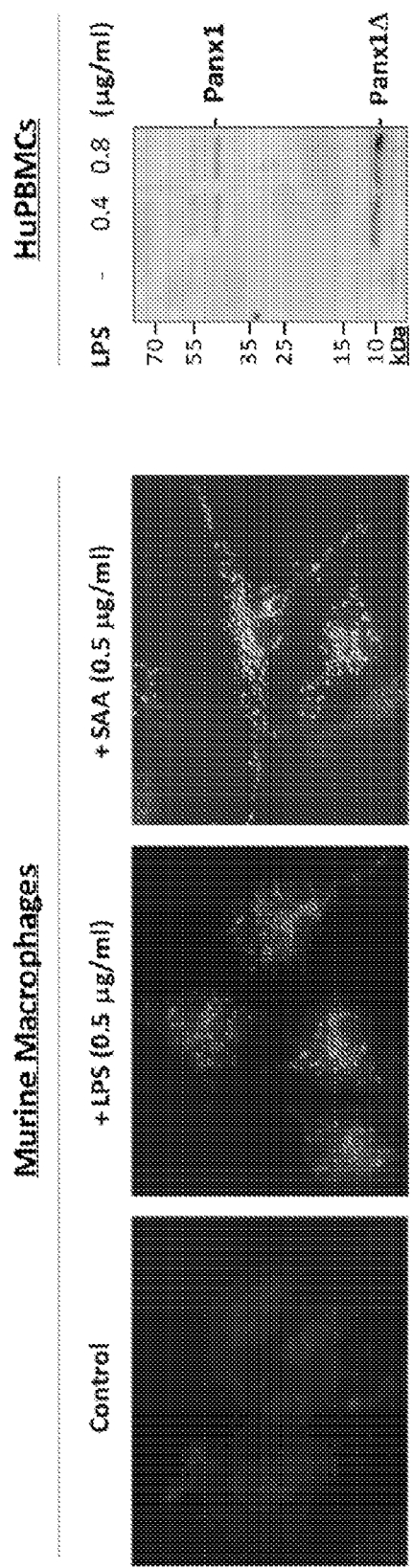

HEMICHANNEL EXTRACELLULAR-DOMAIN SPECIFIC AGENTS FOR TREATING ISCHEMIA-REPERFUSION INJURY

CROSS-REFERENCE TO RELATED APPLICATIONS

This application is a divisional of U.S. patent application Ser. No. 15/748,776, filed Jan. 30, 2018, which is a U.S. national stage of PCT International Patent Application No. PCT/US2016/045284, filed Aug. 3, 2016, which claims the benefit of U.S. Provisional Application No. 62/201,759, filed Aug. 6, 2015, the contents of each of which are hereby incorporated by reference in their entirety.

STATEMENT OF GOVERNMENT SUPPORT

This invention was made with government support under grant numbers GM063075 and AT005076 awarded by the National Institutes of Health. The government has certain rights in the invention.

BACKGROUND OF THE INVENTION

Throughout this application various patents and other publications are referred to by number in parenthesis. Full citations for the references may be found at the end of the specification. The disclosures of these references and all patents, patent application publications and books referred to herein are hereby incorporated by reference in their entirety into the subject application to more fully describe the art to which the subject invention pertains.

Bacterial infection and sepsis are the most common causes of death in the intensive care unit, annually claiming >225,000 victims in the U.S. alone. The pathogenesis of sepsis remains poorly understood, but is attributable to dysregulated systemic inflammation propagated by innate immune cells (IMCs) in response to microbial infections (1,2) and is partly attributable to dysregulated inflammatory responses sustained by proinflammatory mediators (e.g., HMGB1, CIRP, and NO). The seminal discovery of HMGB1 as a late mediator of lethal systemic inflammation (LSI) (Wang et al., Science, 285: 248-51, 1999) has prompted an investigation of the intricate mechanisms underlying the pharmacological modulation of HMGB1 secretion.

The present invention addresses the need for improved pharmacological treatment of sepsis, including by modulation of HMGB1 secretion via hemichannel activity.

SUMMARY OF THE INVENTION

A method is provided of treating sepsis or endotoxemia in a subject or of reducing or inhibiting development of sepsis in a subject, the method comprising administering to the subject an amount of an antagonist of a Panx1 hemichannel protein or an amount of an antagonist of a Cx43 hemichannel protein sufficient to treat sepsis or endotoxemia, or sufficient to reduce or inhibit development of sepsis.

Also provided is a method of treating sepsis or endotoxemia in a subject or of reducing or inhibiting development of sepsis in a subject, the method comprising administering to the subject an amount of an inhibitor of a Panx1 hemichannel protein expression or an amount of an inhibitor of a Cx43 hemichannel protein expression sufficient to treat sepsis or endotoxemia, or sufficient to reduce or inhibit development of sepsis.

A method of treating ischemia-reperfusion injury in a subject or of reducing or inhibiting development of an ischemia-reperfusion injury in a subject, the method comprising administering to the subject an amount of an antagonist of a Cx43 hemichannel protein sufficient to treat ischemia-reperfusion injury in a subject, or reduce or inhibit development of ischemia-reperfusion injury, in a subject.

Additional objects of the invention will be apparent from the description which follows.

BRIEF DESCRIPTION OF THE DRAWINGS

FIG. 2A-2C. CBX effectively suppressed LPS-induced HMGB1 secretion and NO production. Primary peritoneal macrophages were stimulated with crude LPS in the absence or presence of CBX for 16 h, and extracellular levels of 2A: HMGB1, 2B: NO, and 2C: TNF were determined by Western blotting, Griess reaction, and ELISA, respectively. AU, arbitrary units. *, $P<0.05$ versus "+LPS alone."

FIG. 3A-3B. CBX and oATP (a P2X7R antagonist) attenuated crude LPS-induced PKR phosphorylation. Primary peritoneal macrophages were stimulated with crude LPS in the absence or presence of CBX (Panel 3A) or oATP (Panel 3B) for 16 h, and cellular levels of total and phosphorylated PKR ("P-PKR") were determined by Western blotting analysis with reference to a house-keeping protein, β-actin.
*, $P<0.05$ vs. "−LPS-CBX"
, $P<0.05$ vs. "+LPS alone."

FIG. 5A-5B. LPS and SAA induce Panx1 expression in murine macrophages and human monocytes. Primary murine peritoneal macrophages (Panel 5A) and human peripheral blood mononuclear cells (HuPBMCs, Panel 5B) were stimulated with crude LPS or SAA for 6 h, and the cellular Panx1 levels were evaluated by immunocytochemistry (Panel 5A) and Western blotting analysis (Panel 5B), respectively.

DETAILED DESCRIPTION OF THE INVENTION

Figure 1:
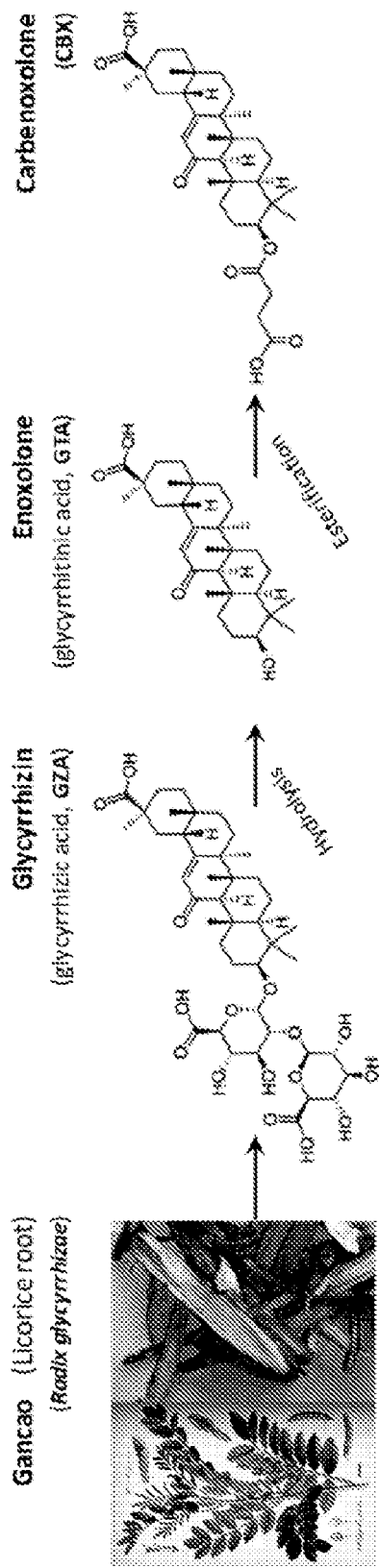
FIG. 1. Chemical structures of a major Gancao component and derivatives. The major Gancao component, glycyrrihizic acid (GZA), can be hydrolyzed into glycyrrhitinic acid (GTA, or enoxolone) by glycaronidase in vivo. In vitro, GTA can be esterified into a succinate ester termed "carbenoxolone" (CBX).

A method is provided of treating sepsis or endotoxemia in a subject or of reducing or inhibiting development of sepsis in a subject, the method comprising administering to the subject an amount of an antagonist of a Panx1 hemichannel protein or an amount of an antagonist of a Cx43 hemichannel protein sufficient to treat sepsis or endotoxemia, or sufficient to reduce or inhibit development of sepsis.

In an embodiment, the amount of the antagonist of a Panx1 hemichannel protein is administered.

In an embodiment, the amount of the antagonist of a Cx43 hemichannel protein is administered.

Also provided is a method of treating sepsis or endotoxemia in a subject or of reducing or inhibiting development of sepsis in a subject, the method comprising administering to the subject an amount of an inhibitor of a Panx1 hemichannel protein expression or an amount of an inhibitor of a Cx43 hemichannel protein expression sufficient to treat sepsis or endotoxemia, or sufficient to reduce or inhibit development of sepsis.

In an embodiment, the amount of the inhibitor of a Panx1 hemichannel protein expression is administered. In an embodiment, the amount of the inhibitor of a Cx43 hemichannel protein expression is administered.

The subject of the method may already have sepsis and the method is to treat sepsis in a subject.

In an embodiment, the method is to reduce or inhibit development of sepsis in a subject.

The subject of the method may already have endotoxemia and the method is to treat endotoxemia in a subject.

A method of treating ischemia-reperfusion injury in a subject or of reducing or inhibiting development of an ischemia-reperfusion injury in a subject, the method comprising administering to the subject an amount of an antagonist of a Cx43 hemichannel protein sufficient to treat ischemia-reperfusion injury in a subject, or reduce or inhibit development of ischemia-reperfusion injury, in a subject. In an embodiment, the antagonist of a Cx43 hemichannel protein is a peptide antagonist. In an embodiment, the peptide antagonist is a peptide having a sequence of an extracellular domain of a Cx43 hemichannel. In an embodiment, the antagonist of a Cx43 hemichannel protein comprises a peptide having the sequence ENVCYD (SEQ ID NO:1) or NVCYDK (SEQ ID NO:2). In an embodiment, the peptide antagonist is overlapping with a protective peptide antagonist which is Gap26 or Gap27 or Gap19. In an embodiment, the peptide antagonist is non-overlapping with a protective peptide antagonist which is Gap26 or Gap27 or Gap19. In an embodiment, the ischemia-reperfusion injury is a hepatic ischemia-reperfusion injury.

In an embodiment of the methods, the antagonist carbenoxolone, glycyrrhizic acid, glycyrrhitinic acid, or monoammonium glycyrrhizinate is administered. In an embodiment, the carbenoxolone, glycyrrhizic acid, glycyrrhitinic acid or monoammonium glycyrrhizinate is free of plant materials. In an embodiment, the carbenoxolone, glycyrrhizic acid, glycyrrhitinic acid or monoammonium glycyrrhizinate is synthetically produced carbenoxolone, glycyrrhizic acid, glycyrrhitinic acid, or monoammonium glycyrrhizinate, respectively.

In an embodiment of the methods, the antagonist of a Cx43 hemichannel protein is a peptide antagonist. In an embodiment, the peptide antagonist is a peptide having the sequence of an extracellular domain of a Cx43 hemichannel. In an embodiment, the peptide antagonist is overlapping with a protective peptide antagonist which is Gap26 or Gap27. In an embodiment, the peptide antagonist is non-overlapping with a protective peptide antagonist which is Gap26 or Gap27 or Gap19.

In an embodiment of the methods, the antagonist of a Panx1 hemichannel protein can be a peptide antagonist. In an embodiment of the methods, the antagonist of a Panx1 hemichannel protein is an anti-Panx1 monoclonal antibody. In an embodiment of the methods, the antagonist of a Cx43 hemichannel protein is an anti-Cx43 monoclonal antibody.

In an embodiment of the methods, the antagonist of a Panx1 hemichannel protein is a small organic molecule of 1500 Da or less. In an embodiment of the methods, the antagonist of a Cx43 hemichannel protein is a small organic molecule of 1500 Da or less.

In an embodiment of the methods, the antagonist of a Cx43 hemichannel protein is not a gap junction antagonist.

In an embodiment, the inhibitor of a Panx1 hemichannel protein expression is an anti-Panx1 siRNA. In an embodiment, the inhibitor of a Cx43 hemichannel protein expression is an anti-Cx43 siRNA.

Figure 6B:
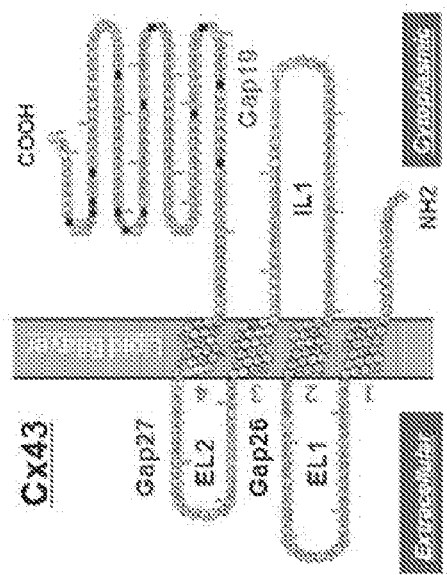
FIG. 6A-6B. Cx43- and Panx1-specific peptide antagonists divergently affect septic lethality. 6A) Balb/C mice were subjected to CLP-induced sepsis, and intro peritoneally administered with saline, or Cx43- or Panx1-specific mimetic peptide (Gap26 (SEQ ID NO:13) or 10Panx (residues 74 to 83 of SEQ ID NO:16); 120 mg/kg) at +6, +18 and +36 h post CLP. Animal survival rates were monitored for two weeks, and the Kaplan-Meier method was used to compare the differences between groups. Shown was a summary of two independent experiments with similar results. *, $P<0.05$ versus saline group. 6B) Membrane topology of Cx43 to indicate the relative localization of three mimetic peptide antagonists: Gap19, Gap26, and Gap27.

Antagonists of the invention can target both types of hemichannel or target one over the other. For example, the small molecule probenecid has been suggested to be a more specific inhibitor for Panx1 (over Cx43) (99); whereas another mimetic peptide, Gap19, corresponding to the intracellular loop (IL1) of Cx43 (FIG. 6B), specifically inhibits Cx43 hemichannel activities (as manifested by ATP release or dye uptake) without affecting Cx43 gap junction communication or Panx1 channel activity (100). Each of these is encompassed by the invention.

In general, the amount of an agent "effective" (e.g., a therapeutic agent, composition, and/or formulation) is an amount effective to achieve a stated effect, to elicit the desired biological response. In some embodiments, a therapeutically effective amount of a substance is an amount that is sufficient, when administered to a subject suffering from or susceptible to a disease, disorder, and/or condition, to treat, diagnose, prevent, and/or delay the onset of one or more symptoms of the disease, disorder, and/or condition. As will be appreciated by those of ordinary skill in this art, and effective amount of a substance may vary depending on such factors as the desired biological endpoint, the substance to be delivered, the pharmacokinetics of the compound, the target cell or tissue, the disease being treated, the mode of administration, and the patient, etc. For example, the effective amount of a composition and/or formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. Those of ordinary skill in the art will appreciate that, commonly, an effective amount will be administered over a series of individual doses. In some embodiments, the term "effective amount" when used in a pharmaceutical context (e.g., pharmaceutically effective amount) means that an agent is present in an amount sufficient to achieve a desired therapeutic effect.

Routes of administration encompassed by the methods of the invention include, but are not limited to, each of the following individual routes, and any subset thereof, auricular, buccal, conjunctival, cutaneous, subcutaneous, endocervical, endosinusial, endotracheal, enteral, epidural, via hemodialysis, interstitial, intrabdominal, intraamniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronary, intradermal, intradiscal, intraductal, intraepidermal, intraesophagus, intragastric, intravaginal, intragingival, intraileal, intraluminal, intralesional, intralymphatic, intramedullary, intrameningeal, intramuscular, intraocular, intraovarian, intraepicardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intraventricular, intravesical, intravitreal, laryngeal, nasal, nasogastric, ophthalmic, oral, oropharyngeal, parenteral, percutaneous, periarticular, peridural, rectal, inhalationally, retrobulbar, subarachnoid, subconjuctival, sublingual, submucosal, topically, transdermal, transmucosal, transplacental, transtracheal, ureteral, urethral, and vaginal administration.

In an embodiment of the methods, the subject is human.

In an embodiment, the Cx43 is Human Cx43 having the following sequence (SEQ ID NO:15):

```
MGDWSALGKLLDKVQAYSTAGGKVWLSVLFIFRILLLGTAVESAWGDEQSA
FRCNTQQPGCENVCYDKSFPISHVRFWVLQIIFVSVPTLLYLAHVFYVMRK
EEKLNKKEEELKVAQTDGVNVDMHLKQIEIKKFKYGIEEHGKVKMRGGLLR
TYIISILFKSIFEVAFLLIQWYIYGFSLSAVYTCKRDPCPHQVDCFLSRPT
EKTIFIIFMLVVSLVSLALNIIELFYVFFKGVKDRVKGKSDPYHATSGALS
PAKDCGSQKYAYFNGCSSPTAPLSPMSPPGYKLVTGDRNNSSCRNYNKQAS
EQNWANYSAEQNRMGQAGSTISNSHAQPFDFPDDNQNSKKLAAGHELQPLA
IVDQRPSSRASSRASSRPRPDDLEI.
```

In an embodiment, the Panx1 is Human Panx1 having the following sequence (SEQ ID NO:16):

```
MAIAQLATEYVFSDFLLKEPTEPKFKGLRLELAVDKMVTCIAVGLPLLLIS
LAFAQEISIGTQISCFSPSSFSWRQAAFVDSYCWAAVQQKNSLQSESGNLP
LWLHKFFPYILLLFAILLYLPPLFWRFAAAPHICSDLKFIMEELDKVYNRA
IKAAKSARDLDMRDGACSVPGVTENLGQSLWEVSESHFKYPIVEQYLKTKK
NSNNLIIKYISCRLLTLIIILLACIYLGYYFSLSSLSDEFVCSIKSGILRN
DSTVPDQFQCKLIAVGIFQLLSVINLVVYVLLAPVVVYTLFVPFRQKTDVL
KVYEILPTFDVLHFKSEGYNDLSLYNLFLEENISEVKSYKCLKVLENIKSS
GQGIDPMLLLTNLGMIKMDVVDGKTPMSAEMREEQGNQTAELQGMNIDSET
KANNGEKNARQRLLDSSC.
```

In an embodiment, the Gap26 has the sequence: VCYDKSFPISHVR (SEQ ID NO:17).

In an embodiment, the Gap27 has the sequence: SRPTEKTIFII (SEQ ID NO:18).

In an embodiment, the Gap19 has the sequence: KQIEIKKFK (SEQ ID NO:19).

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

Experimental Results

Introduction

It was recently shown that ultrapure lipopolysaccharide (LPS) (10 µg/ml) can stimulate macrophages to produce early cytokines (e.g., TNF), but completely fails to trigger HMGB1 secretion unless the initial LPS priming is accompanied by a second stimulus (e.g., ATP) (43,44). Similarly, ATP itself is unable to induce HMGB1 secretion without prior LPS exposure (43), even though it can facilitate PKR phosphorylation (44) and inflammasome activation (46-48). In contrast, prolonged stimulation with the commonly-used (and presumably also more clinically relevant) crude LPS (containing <1% bacterial proteins and nucleic acids such as CpG-DNA) led to dramatic PKR phosphorylation (49) and HMGB1 secretion (21).

Macrophages/monocytes release ATP through the membrane hemichannels composed of connexins (Cx) or pannexins (Panx). Despite of the lack of amino acid sequence homology, Cx43 and Panx1 exhibit similar membrane topology by carrying four transmembrane domains, one intracellular loop (along with the N and C termini), and two extracellular loops. Although both can oligomerize to form the hexameric half channel (or "hemichannel") only Cx43 hemichannels can dock with the hemichannels on adjacent cells to form gap junction channels (GJC) that facilitate intercellular communication in the heart, vasculature, and brain. Nevertheless, both Cx43 and Panx1 hemichannels may provide a temporal mode of ATP release from activated innate immune cells (e.g., monocytes, macrophages and neutrophils) (51,52). For instance, Panx1 has been shown to contribute to ATP release from apoptotic cells (53,54), because pharmacological inhibition (by a Gancao component derivative, CBX, >100 µM) or genetic knock-down of PANX1 uniformly attenuated ATP liberation. It has been suggested that ATP contributes to inflammasome activation through activating the purinergic P2X7 receptor (P2X7R) (50). The activation of P2X7R results in an immediate (within milliseconds) opening of ATP-gated P2X7R channel permeable for small cations ($Ca^{2+}$), followed by a gradual recruitment and opening (over seconds to minutes) of larger Panx1 hemichannels, allowing passage of larger anionic molecules up to 900 Da (e.g., ATP) (55-57). This Panx1-mediated feed-forward ATP release contributes to the LPS-stimulated inflammasome activation (58) and subsequent inflammasome-dependent cytokine release (46-48,59,60).

Gancao (Radix glycyrrhizae, or licorice) has been traditionally used in the treatment of peptic ulcer, hepatic injury, and hepatitis, but its protective mechanisms remain elusive. Data disclosed herein indicates that carbenoxolone (CBX), a derivative of the major Gancao component, glycyrrhizin (glycyrrhizic acid, GZA), dose-dependently abrogated LPS-induced PKR (dsRNA-activated protein kinase R) phosphorylation and HMGB1 secretion, and rescues mice from lethal sepsis (induced by cecal ligation and puncture, CLP) even if given in a delayed fashion.

EXAMPLES

Multiple herbal components were screened for activities in inhibiting LPS-induced PKR activation and HMGB1 secretion. Gancao (Radix glycyrrhizae) has been traditionally used for many centuries in the treatment of various inflammatory ailments including peptic ulcer, hepatitis, and pulmonary bronchitis. Its anti-inflammatory properties are attributable to a major component, glycyrrhizin (glycyrrhizic acid, GZA, FIG. 1), which has been proven beneficial in animal models of hepatitis (61, hepatic ischemia/reperfusion (I/R) (62,63), toxin-induced liver injury (64,65), endotoxemia (66,67), and colitis (68). The replacement of the glucuronic acid in GZA by succinic acid gives rise to a new compound, carbenoxolone (CBX, FIG. 1), a drug previously prescribed for patients with esophageal ulceration and other inflammation ailments (69).

Since its inception, CBX has been shown to dose-dependently inhibit a variety of biological activities including the Cx43 gap junctions ($EC_{50}$=50-100 µM) and the Panx1 hemichannels ($EC_{50}$=1-4 µM) (70,71). For instance, it was previously shown that CBX (10 µM) effectively inhibited the Panx1 hemichannel-mediated ATP release in response to hypoxia (72), sheer stress (73), and low oxygen tension (74). Furthermore, CBX can inhibit LPS-induced dye uptake (55,75), and confer protection against LPS-induced acute lung injury (76), and cerebral ischemic injury (77). Herein it is disclosed that CBX remarkably inhibited endotoxin-induced nitric oxide production and HMGB1 secretion in macrophage cultures (FIG. 2), confirming Gancao's anti-inflammatory properties. However, it is unlikely that CBX inhibits the LPS-induced HMGB1 secretion through impairing the Cx43 gap junctions, because macrophages do not form gap junctions with themselves, and the concentrations of CBX used to block gap junctions (e.g., 50-100 µM) in other cell types are much higher than those (e.g., 5-10 µM) used to abrogate LPS-induced HMGB1 secretion in macrophages (49). It is not known, however, if CBX attenuates Cx43 hemichannel-mediated ATP release, thereby affecting subsequent PKR activation and HMGB1 secretion. To test this possibility, it was determined whether CBX affected membrane hemichannel activities by measuring the cellular uptake of an anionic dye, Lucifer Yellow (LY, MW=444 Da). In quiescent macrophages, approximately 2% cells displayed diffuse fluorescent signal after LY incubation, whereas prolonged LPS stimulation elevated the number of LY-positive cells to ~16%, suggesting that LPS increased macrophage hemichannel activities (49). However, CBX significantly reduced the number of LY-positive cells to 6-8%, suggesting that CBX effectively inhibits LPS-induced HMGB1 secretion by blocking macrophage hemichannel activities.

One of the key ATP receptors, P2X7R may be important in LPS-induced HMGB1 secretion because a specific P2X7R antagonist, oATP, similarly inhibited LPS-induced LY-uptake and HMGB1 secretion (data not shown). In light of the roles of P2X7R and PKR in LPS/ATP-induced inflammasome activation (44,58), it was tested whether CBX and P2X7R antagonists (e.g., oATP) have an effect on LPS-induced PKR activation in primary macrophage cultures. Remarkably, prolonged stimulation with crude LPS (containing trace amounts of bacterial proteins and nucleic acids) resulted in a >2-fold increase of total PKR protein levels, but a more robust (>8-fold) elevation of phosphorylated PKR levels (FIG. 3A, 3B). Furthermore, this LPS-induced elevation of PKR expression and phosphorylation was significantly attenuated both by CBX (FIG. 3A) and oATP (FIG. 3B), suggesting an important role for hemichannels and PKR activation in LPS-induced HMGB1 secretion.

Figure 4:
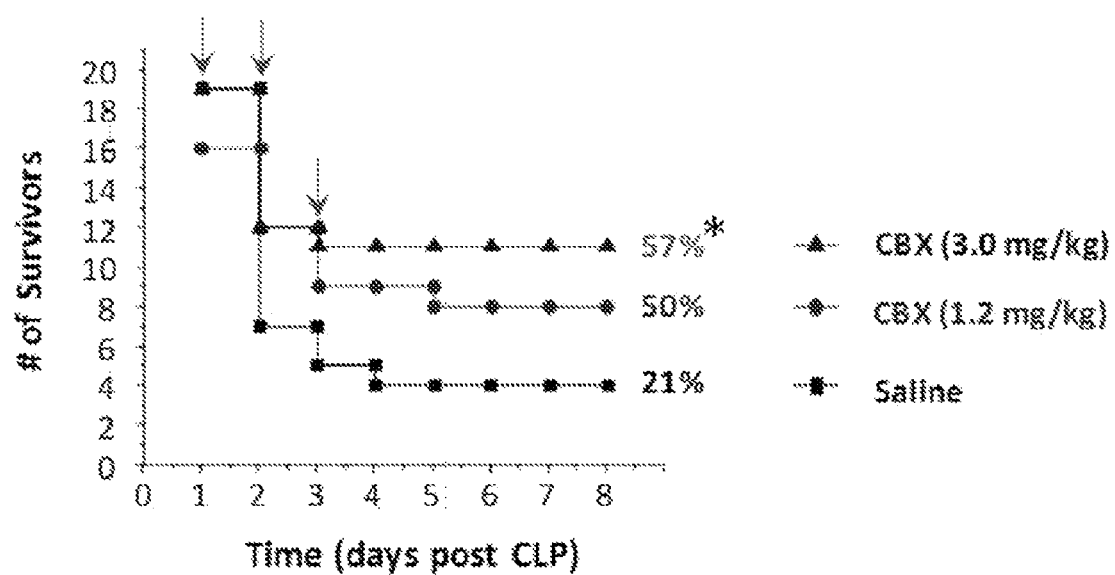
FIG. 4. Delayed administration of CBX rescued mice from lethal sepsis. Balb/C mice were subjected to lethal sepsis (induced by CLP), and intraperitoneally administered with saline or CBX at indicated doses at +24, +48 and +72 h post CLP. Animal survival rates were monitored, and the Kaplan-Meier method was used to compare the differences between groups. Arrows indicate time points of drug administration. *, $P<0.05$ versus saline control group.

Given the pathogenic role of HMGB1 in lethal sepsis (32), the therapeutic potential of CBX was explored using a clinically relevant animal model of polymicrobial sepsis induced by CLP. The first dose of CBX was given 24 h after CLP, a time point at which mice developed clear signs of sepsis including lethargy, diarrhea, and piloerection. Repeated administration of CBX beginning 24 h after the onset of sepsis (followed by additional doses at 48 and 72 h post CLP) conferred a dose-dependent and significant protection (FIG. 4), supporting CBX as a therapeutic in the treatment of sepsis. Data obtained here (not shown) indicates that CBX binds to HMGB1 A-box with an affinity >20-fold higher than that of the most well-known HMGB1 inhibitor, GZA (111).

It was previously unknown whether the pharmacological targets of CBX, such as Panx1 and Cx43, also occupy a pathogenic role in LSI possibly by facilitating ATP efflux, PKR activation and HMGB1 secretion. It was investigated whether prolonged stimulation with crude LPS or other HMGB1 secretion stimuli (such as SAA or CIRP) may upregulate the expression of Panx1 and/or Cx43 hemichannel, which facilitate ATP efflux, PKR phosphorylation, and subsequent HMGB1 secretion, thereby contributing to the pathogenesis of LSI. A hypothesis was proposed that exogenous PAMPs (LPS) and endogenous proinflammatory mediators (SAA or CIRP) regulate HMGB1 secretion through stimulating Panx1 and/or Cx43 hemichannel expression and PKR phosphorylation. In light of the important role of Cx43 and Panx1 in ATP efflux, in conjunction with the requirement of ATP for ultrapure LPS-induced HMGB1 secretion, it was desirable to determine whether crude LPS and other key HMGB1 secretion stimuli (e.g., CIRP and SAA) can uniformly modulate hemichannel expression and PKR/STAT1 phosphorylation.

Primary murine macrophages and human monocytes were employed to investigate the mechanisms underlying the regulation of HMGB1 secretion by various inflammatory stimuli. Primary peritoneal macrophages were isolated from Balb/C mice (male, 7-8 weeks, 20-25 grams) at 2-3 days after intraperitoneal injection of 2 ml thioglycollate broth (4%, Difco, Detroit, Mich.) as previously described (23,78). Human peripheral blood mononuclear cells (HuPBMCs) were isolated from human blood purchased from the New York (Long Island) Blood Bank (Melville, N.Y.) by density gradient centrifugation through Ficoll (Ficoll-Paque PLUS, Pharmacia, Piscataway, N.J.) as previously described (23, 78,79). At 80-90% confluence, macrophage/monocyte cultures will be stimulated with divergent stimuli: ultrapure and crude LPS, CIRP 14, SAA (PeproTech, Cat. No. 300-13) at different concentrations and for various time periods (0, 6, 12, and 18 h). The expression levels of Cx43 or Panx1 hemichannel proteins in macrophage/monocyte cultures are determined by Western blotting or immunocytochemistry techniques as previously described (21,23,80).

The expression of hemichannel proteins might be regulated differentially in immune versus non-immune cells. For instance, LPS down-regulates Cx43 expression in the liver and heart (81), but up-regulates it in the kidney, lung (82), and IMCs (83,84). Accordingly, prolonged stimulation with crude LPS, SAA, or CIRP will similarly upregulate Cx43 and Panx1 hemichannel proteins in monocyte/macrophage cultures. Indeed, it was found that both LPS and SAA effectively elevated cellular levels of Panx1 in both murine macrophages (FIG. 5A) and human monocytes (FIG. 5B). Consistent with the notion that the enzymatic cleavage of Panx1 by caspase 3 in apoptotic cells is required for activation and opening of Panx1 hemichannels (53), it was found that the upregulation of Panx1 was accompanied by the appearance of a smaller molecular weight (10 kDa) band (FIG. 5B), possibly indicative of a Panx1 degradation product.

Roles of hemichannels in the pathogenesis of LSI: The data obtained here indicated that LPS and SAA unregulated the expression of Panx1 and Cx43 in primary murine macrophages and human monocytes. This is interesting in view of a recent study that suggested conditional knockout of Cx43 in the CD11c-expressing leukocytes rendered mice more susceptible to lethal endotoxemia (105), reinforcing the notion of a beneficial role of Cx43 in alveolar macrophage-epithelium gap junction communication (GJCs). In light of the possible roles of these hemichannel proteins in ATP-dependent PKR activation and HMGB1 secretion, it was determined whether alterations of these hemichannel activities (by using mimetic peptide antagonists, neutralizing antibodies, or herbal inhibitors such as GZA) or protein levels (by gene KO) affect animal survival in endotoxemia and CLP-induced sepsis.

Sepsis is commonly simulated in animals by intraperitoneally administering a bolus and known amount of endotoxin (endotoxemia), or by surgically inducing peritonitis via perforating the cecum—a technique known as cecal ligation and puncture (CLP) as previously described (21,78, 94,95). To understand the possible role of hemichannel proteins in LSI, male Balb/C mice (7-8 weeks, 20-25 g) are subjected to lethal endotoxemia or sepsis, and a wide range of hemichannel inhibitors (e.g., mimetic peptide antagonists, and herbal component, GZA) is injected intraperitoneally at various doses and time points (0.5, 12, and 24 h) after the onset of endotoxemia or sepsis. Their effects on the outcomes of LSI are assessed by comparing the long-term (two-week) survival rates between the anti-hemichannel-treated groups with vehicle-treated controls.

Figure 6A:
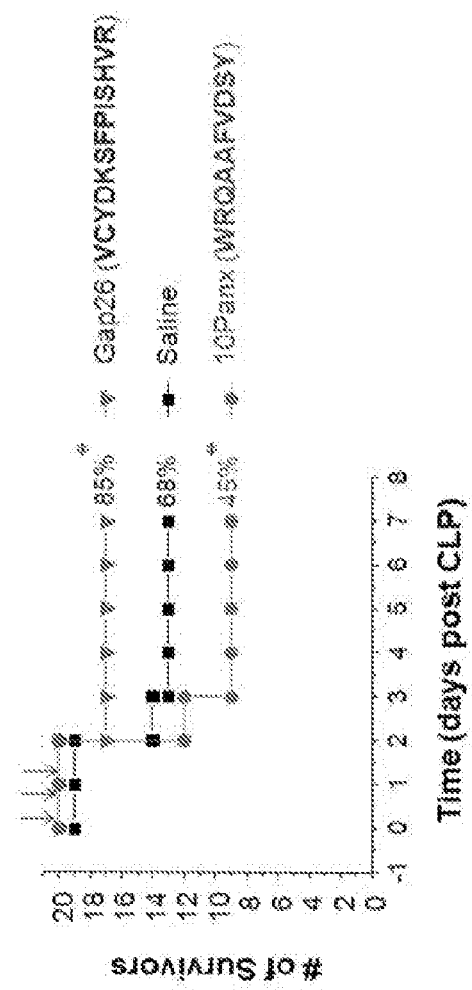
Figure 7:
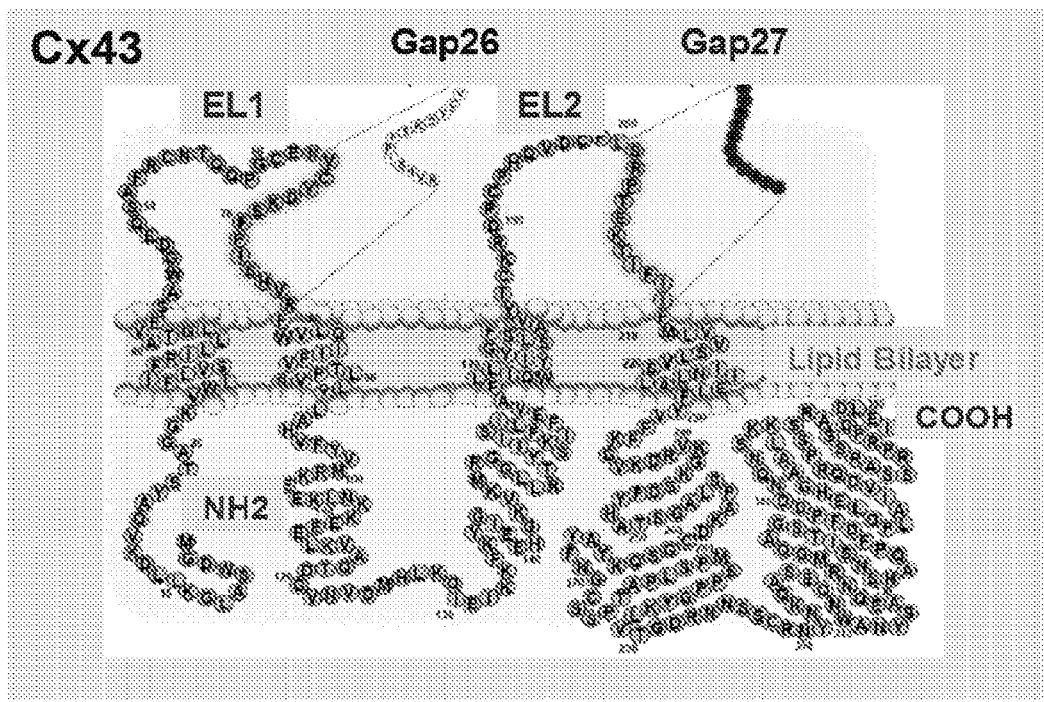
FIG. 7. Synthesis of small Cx43 peptide antagonists. Peptides were synthesized (ten peptides as shown in the bottom panel) corresponding to the extracellular loop 1 (EL1) of connexin 43 (Cx43). These peptides were screened for their activities in inhibiting macrophage hemichannel activities and protective efficacy in animal models of infection—or injury-elicited inflammatory diseases. (P1 is SEQ ID NO:3; P2 is SEQ ID NO:4; P3 is SEQ ID NO:5; P4 is SEQ ID NO:6; P5 is SEQ ID NO:1; P6 is SEQ ID NO:2; P7 is SEQ ID NO:7; P8 is SEQ ID NO:8; P9 is SEQ ID NO:9; and P10 is SEQ ID NO:10). The CX43 sequence shown in the top panel is SEQ ID NO:11. The CX43 extracellular loop 1 is SEQ ID NO:12. The portion of CX43 extracellular loop 1 having the sequence known as Gap26 (SEQ ID NO:13) is residues 22 through 34 of SEQ ID NO:12.
Figure 8:
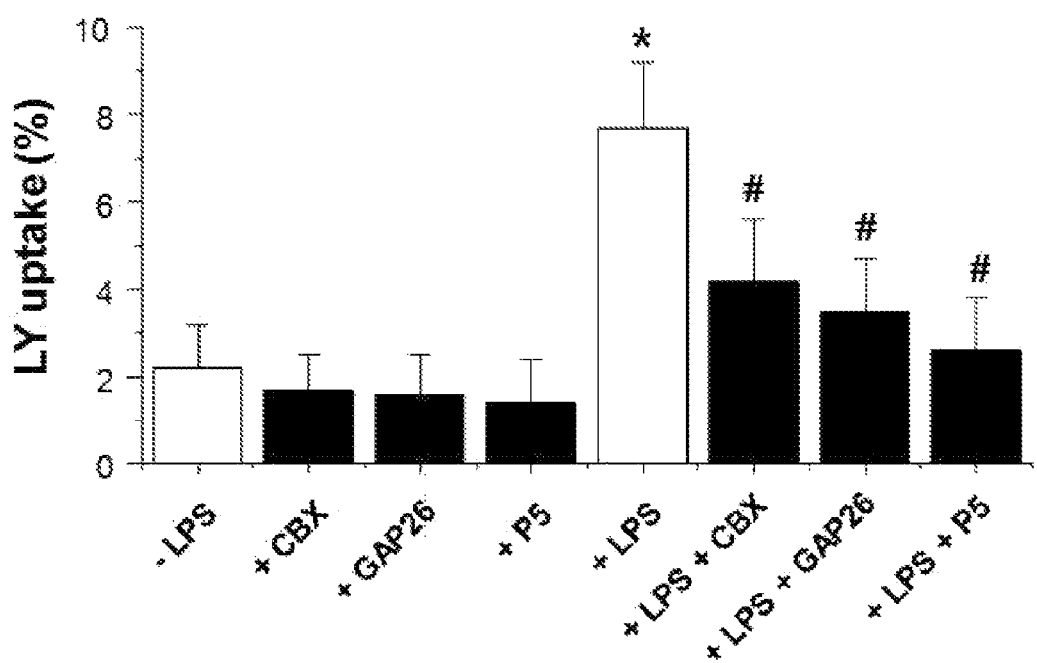
FIG. 8. P5 peptide (SEQ ID NO:1) significantly inhibited bacterial endotoxin-induced dye uptake. The Lucifer Yellow dye uptake was used to measure the connexin 43-gated hemichannel activities. Briefly, RAW 264.7 cells were stimulated with LPS in the absence or presence of CBX or other Cx43 peptide antagonists (GAP26 (SEQ ID NO:13) or P5) for 16 h. Subsequently, cell cultures were incubated with Lucifer Yellow (LY, 1 mg/ml) for 15 min, and fixed with 2% paraformaldehyde following three extensive washes with 1× PBS. The number of cells with diffused fluorescent signals was counted under a fluorescence microscope. The cells containing punctuate fluorescent signals were excluded, as the punctuate signals likely resulted from phagocytosis (rather than passive diffusion through Cx43 hemichannels) of the LY dye.
Figure 9:
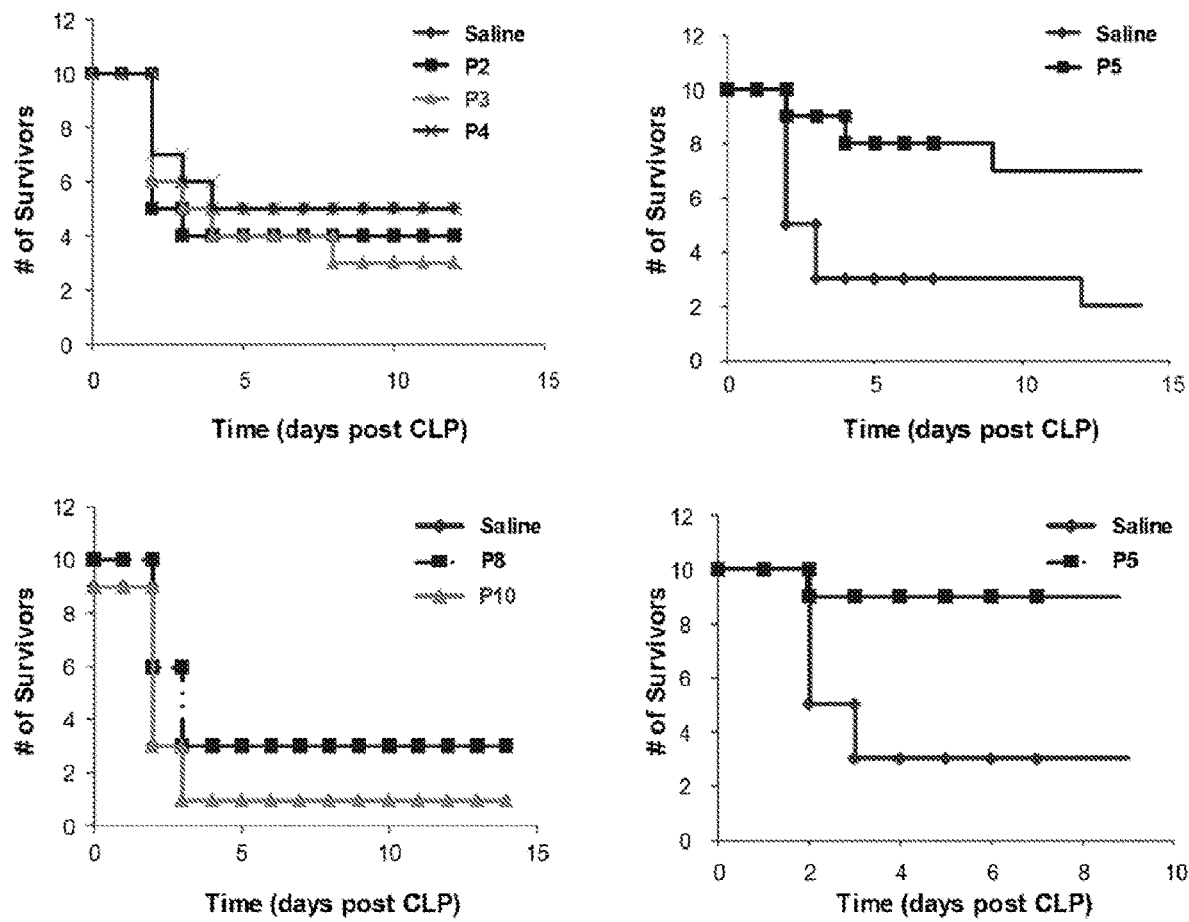
FIG. 9. P5 peptide significantly attenuated lethal sepsis. Balb/C mice (male, 20-25 g, 7-10 weeks) were subjected to lethal sepsis by CLP, and intraperitoneally administered with control saline (0.2 ml/mouse) or indicated peptide (10.0 mg/kg) at +0.5, +24 hours post CLP. Animal survival was assessed for up to two weeks, and the Kaplan-Meier method was used to compare the differences in mortality rates between groups. A P value <0.05 was considered statistically significant. Note that peptide #2, #3, #4, #8, #9, and #10 did not confer protection against lethal sepsis. However, P5 (SEQ ID NO:1) dramatically and significantly increased animal survival. To a lesser extent, P6 (SEQ ID NO:2) also exhibited protective effect in animal models of lethal sepsis (data not shown).
Figure 10:
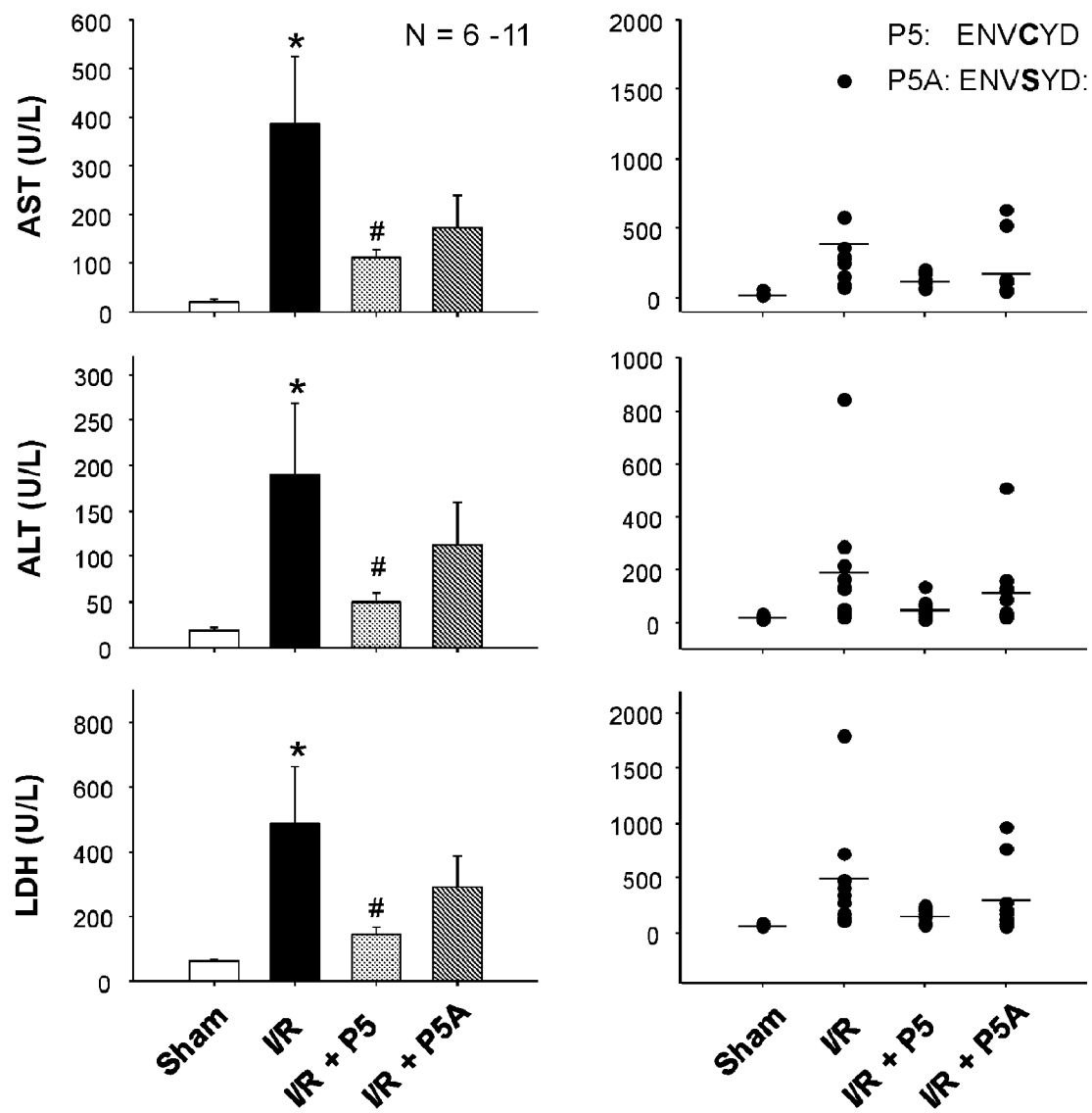
FIG. 10. Intravenous administration of Cx43 peptide antagonist conferred protection against hepatic ischemia/ reperfusion (I/R) injury. Male C57BL/6 mice (20-25 g) were subjected to hepatic ischemia/reperfusion by temporally clamping the hepatic artery and portal vein for 60 minutes, which typically produced ischemia in 70% of the liver. At the beginning of the reperfusion, 0.2 ml saline, P5 (ENVCYD; 10.0 mg/kg BW) or P5A (ENVSYD (SEQ ID NO:14); 10.0 mg/kg BW) was injected via the internal jugular vein. At 24 h after the onset of ischemia, animals were euthanized to harvest blood to measure serum levels of hepatic injury markers such as alanine aminotransferase (ALT) and aspartate aminotransferase (AST) using commercial kits. Note that P5 peptide promoted significant protection against I/R injury. *, P<0.05 versus sham control; #, P<0.05 versus Saline group ("I/R").

To modulate the hemichannel activities, various mimetic "gap" peptides have been designed to mimic the extracellular loops of Cx43 and Panx1. For instance, Gap26 and Gap27 mimic a short stretch of amino acids on the first and second extracellular loops (EL1 and EL2, FIG. 6B), and are expected to interact with the extracellular loops of the Cx43 (96), thereby inhibiting Cx43 hemichannel activities or Cx43 gap junction formation. Similarly, a Panx1-specific mimetic inhibitory peptide, 10Panx, has been shown to selectively attenuate P2X7R-induced Panx1 hemichannel activation (97,98). It was found that the Panx1-specific mimetic peptide, 10Panx, reproducibly exacerbated CLP-induced animal lethality when given repetitively at a dose of 120 mg/kg (FIG. 6A). In a sharp contrast, repetitive administration of a Cx43-specific mimetic peptide (Gap26, at +6 and +18, and 36 h post CLP; 120 mg/kg), promoted a reproducible and significant protection against lethal sepsis (FIG. 6A).

To further confirm the pathogenic role of Cx43 in LSI, monoclonal antibodies (MAbs) are generated targeting extracellular loops of Cx43, and it is tested whether Cx43-specific MAbs similarly protects animals against lethal sepsis. Multiple hyridomas have been generated by this laboratory that produce Gap26-reactive antibodies, and the antibodies will be screened for their activities in inhibiting hemichannel activities using the LY dye uptake or ATP release assays (49).

Peptides were synthesized (ten peptides as shown in the bottom panel) corresponding to the extracellular loop 1 (EL1) of connexin 43 (Cx43). These peptides were screened for their activities in inhibiting macrophage hemichannel activities and protective efficacy in animal models of infection- or injury-elicited inflammatory diseases.

P5 peptide (SEQ ID NO:1) significantly inhibited bacterial endotoxin-induced dye uptake. The Lucifer Yellow dye uptake was used to measure the connexin 43-gated hemichannel activities. Briefly, RAW 264.7 cells were stimulated with LPS in the absence or presence of CBX or other Cx43 peptide antagonists (GAP26 (SEQ ID NO:13) or P5) for 16 h. Subsequently, cell cultures were incubated with Lucifer Yellow (LY, 1 mg/ml) for 15 min, and fixed with 2% paraformaldehyde following three extensive washes with 1×PBS. The number of cells with diffused fluorescent signals was counted under a fluorescence microscope. The cells containing punctuate fluorescent signals were excluded, as the punctuate signals likely resulted from phagocytosis (rather than passive diffusion through Cx43 hemichannels) of the LY dye. P5 peptide also significantly attenuated lethal sepsis. Balb/C mice (male, 20-15 g, 7-10 weeks) were subjected to lethal sepsis by CLP, and intraperitoneally administered with control saline (0.2 ml/mouse) or indicated peptide (10.0 mg/kg) at +0.5, +24 hours post CLP. Animal survival was assessed for up to two weeks, and the Kaplan-Meier method was used to compare the differences in mortality rates between groups. A P value <0.05 was considered statistically significant. Note that peptide #2, #3, #4, #8, #9, and #10 did not confer protection against lethal sepsis. However, P5 (SEQ ID NO:1) dramatically and significantly increased animal survival. To a lesser extent, P6 (SEQ ID NO:2) also exhibited protective effect in animal models of lethal sepsis (data not shown).

Intravenous administration of Cx43 peptide antagonist conferred protection against hepatic ischemia/reperfusion (I/R) injury. Male C57BL/6 mice (20-25 g) were subjected to hepatic ischemia/reperfusion by temporally clamping the hepatic artery and portal vein for 60 minutes, which typically produced ischemia in 70% of the liver. At the beginning of the reperfusion, 0.2 ml saline, P5 (ENVCYD, 10.0 mg/kg BW) or P5A (ENVSYD (SEQ ID NO:14), 10.0 mg/kg) was injected via the internal jugular vein. At 24 h after the onset of ischemia, animals were euthanized to harvest blood to measure serum levels of hepatic injury markers such as alanine aminotransferase (ALT) and aspartate aminotransferase (AST) using commercial kits. Note that P5 peptide promoted significant protection against I/R injury. *, P<0.05 versus sham control; #, P<0.05 versus Saline group ("I/R").

REFERENCES

1. Hotchkiss, R. S., Coopersmith, C. M., McDunn, J. E. & Ferguson, T. A. The sepsis seesaw: tilting toward immunosuppression. Nat. Med. 15, 496-497 (2009).
2. Koay, M. A. et al. Macrophages are necessary for maximal nuclear factor-kappa B activation in response to endotoxin. Am. J. Respir. Cell Mol. Biol. 26, 572-578 (2002).
3. Brightbill, H. D. et al. Host defense mechanisms triggered by microbial lipoproteins through toll-like receptors. Science 285, 732-736 (1999).
4. Poltorak, A. et al. Defective LPS signaling in C3H/HeJ and C57BL/10ScCr mice: mutations in Tlr4 gene. Science 282, 2085-2088 (1998).
5. Hemmi, H. et al. A Toll-like receptor recognizes bacterial DNA. Nature 408, 740-745 (2000).
6. Zingarelli, B. Peptidoglycan is an important pathogenic factor of the inflammatory response in sepsis. Crit Care Med. 32, 613-614 (2004).
7. Akira, S. & Takeda, K. Toll-like receptor signalling. Nat. Rev. Immunol. 4, 499-511 (2004).
8. Baggiolini, M. & Loetscher, P. Chemokines in inflammation and immunity. Immunol. Today 21, 418-420 (2000).
9. Balkwill, F. Cytokines—soluble factors in immune responses. Curr. Opin. Immunol. 1, 241-249 (1988).
10. Wang, H., Czura C. J. & Tracey K. J. The Cytokine Handbook. Thomson, A. & Lotze, M. T. (eds.), pp. 837-860 (Academic Press, Oxford, 2003).
11. Dinarello, C. A. Biologic basis for interleukin-1 in disease. Blood 87, 2095-2147 (1996).
12. Heinzel, F. P. The role of IFN-gamma in the pathology of experimental endotoxemia. J Immunol 145, 2920-2924 (1990).
13. Varma, T. K., Lin, C. Y., Toliver-Kinsky, T. E. & Sherwood, E. R. Endotoxin-induced gamma interferon production: contributing cell types and key regulatory factors. Clin. Diagn. Lab Immunol. 9, 530-543 (2002).
14. Qiang, X. et al. Cold-inducible RNA-binding protein (CIRP) triggers inflammatory responses in hemorrhagic shock and sepsis. Nat. Med. 19, 1489-1495 (2013).
15. MacMicking, J. D. et al. Altered responses to bacterial infection and endotoxic shock in mice lacking inducible nitric oxide synthase. Cell. %19; 81, 641-650 (1995).
16. Tracey, K. J. et al. Anti-cachectin/TNF monoclonal antibodies prevent septic shock during lethal bacteraemia. Nature 330, 662-664 (1987).
17. Dinarello, C. A. & Thompson, R. C. Blocking IL-1: interleukin 1 receptor antagonist in vivo and in vitro. Immunol Today 12, 404-410 (1991).
18. Romero, C. R. et al. The role of interferon-gamma in the pathogenesis of acute intra-abdominal sepsis. J. Leukoc. Biol. 88, 725-735 (2010).
19. Petros, A. et al. Effects of a nitric oxide synthase inhibitor in humans with septic shock. Cardiovasc. Res. 28, 34-39 (1994).
20. Vincent, J. L., Zhang, H., Szabo, C. & Preiser, J. C. Effects of nitric oxide in septic shock. Am. J. Respir. Crit Care Med 161, 1781-1785 (2000).
21. Wang, H. et al. HMG-1 as a late mediator of endotoxin lethality in mice. Science 285, 248-251 (1999).
22. Ivanov, S. et al. A novel role for HMGB1 in TLR9-mediated inflammatory responses to CpG-DNA. Blood. 110, 1970-1981 (2007).
23. Rendon-Mitchell, B. et al. IFN-gamma Induces High Mobility Group Box 1 Protein Release Partly Through a TNF-Dependent Mechanism. J Immunol 170, 3890-3897 (2003).
24. Hudgins, L. C. et al. A single intravenous dose of endotoxin rapidly alters serum lipoproteins and lipid transfer proteins in normal volunteers. J. Lipid Res. 44, 1489-1498 (2003).
25. Ganapathi, M. K., Rzewnicki, D., Samols, D., Jiang, S. L. & Kushner, I. Effect of combinations of cytokines and hormones on synthesis of serum amyloid A and C-reactive protein in Hep 3B cells. J. Immunol. 147, 1261-1265 (1991).
26. Yamada, T., Wada, A., Itoh, K. & Igari, J. Serum amyloid A secretion from monocytic leukaemia cell line THP-1 and cultured human peripheral monocytes. Scand. J. Immunol. 52, 7-12 (2000).
27. Ramadori, G., Sipe, J. D., Dinarello, C. A., Mizel, S. B. & Colten, H. R. Pretranslational modulation of acute phase hepatic protein synthesis by murine recombinant interleukin 1 (IL-1) and purified human IL-1. J. Exp. Med. 162, 930-942 (1985).
28. Jiang, S. L., Lozanski, G., Samols, D. & Kushner, I. Induction of human serum amyloid A in Hep 3B cells by IL-6 and IL-1 beta involves both transcriptional and post-transcriptional mechanisms. J. Immunol. 154, 825-831 (1995).
29. Maury, C. P., Enholm, E. & Teppo, A. M. Is interferon an "inducer" of serum amyloid A? N. Engl. J. Med. 309, 1060-1061 (1983).
30. McAdam, K. P. & Sipe, J. D. Murine model for human secondary amyloidosis: genetic variability of the acute-phase serum protein SAA response to endotoxins and casein. J. Exp. Med. 144, 1121-1127 (1976).

31. Wang, Q. et al. Endotoxemia in mice stimulates production of complement C3 and serum amyloid A in mucosa of small intestine. Am. J. Physiol. 275, R1584-R1592 (1998).
32. Yang, H. et al. Reversing established sepsis with antagonists of endogenous high-mobility group box 1. Proc Natl Acad Sci USA 101, 296-301 (2004).
33. Wang, H., Yang, H., Czura, C. J., Sama, A. E. & Tracey, K. J. HMGB1 as a Late Mediator of Lethal Systemic Inflammation. Am J Respir Crit Care Med 164, 1768-1773 (2001).
34. Qin, S. et al. Role of HMGB1 in apoptosis-mediated sepsis lethality. J Exp. Med 203, 1637-1642 (2006).
35. Wang, H., Yang, H. & Tracey, K. J. Extracellular role of HMGB1 in inflammation and sepsis. J Intern. Med 255, 320-331 (2004).
36. Wang, H., Zhu, S., Zhou, R., Li, W. & Sama, A. E. Therapeutic potential of HMGB1-targeting agents in sepsis. Expert. Rev. Mol. Med 10, e32 (2008).
37. Wang, H., Ward, M. F. & Sama, A. E. Novel HMGB1-inhibiting therapeutic agents for experimental sepsis. Shock. 32, 348-357 (2009).
38. Lu, B. et al. Molecular mechanism and therapeutic modulation of high mobility group box 1 release and action: an updated review. Expert. Rev. Clin. Immunol. 10, 713-727 (2014).
39. Wang, H., Ward, M. F. & Sama, A. E. Targeting HMGB1 in the treatment of sepsis. Expert. Opin. Ther. Targets. 18, 257-268 (2014).
40. Gardella, S. et al. The nuclear protein HMGB1 is secreted by monocytes via a non-classical, vesicle-mediated secretory pathway. EMBO Rep 3, 955-1001 (2002).
41. Bonaldi, T. et al. Monocytic cells hyperacetylate chromatin protein HMGB1 to redirect it towards secretion. EMBO J 22, 5551-5560 (2003).
42. Lu, B. et al. JAK/STAT1 signaling promotes HMGB1 hyperacetylation and nuclear translocation. Proc. Natl. Acad. Sci. U.S.A. 111, 3068-3073 (2014).
43. Lamkanfi, M. et al. Inflammasome-dependent release of the alarmin HMGB1 in endotoxemia. J. Immunol. 185, 4385-4392 (2010).
44. Lu, B. et al. Novel role of PKR in inflammasome activation and HMGB1 release. Nature. 488, 670-674 (2012).
45. Hett, E. C. et al. Chemical genetics reveals a kinase-independent role for protein kinase R in pyroptosis. Nat. Chem. Biol. 9, 398-405 (2013).
46. Mehta, V. B., Hart, J. & Wewers, M. D. ATP-stimulated release of interleukin (IL)-1beta and IL-18 requires priming by lipopolysaccharide and is independent of caspase-1 cleavage. J. Biol. Chem. 276, 3820-3826 (2001).
47. Griffiths, R. J., Stam, E. J., Downs, J. T. & Otterness, I. G. ATP induces the release of IL-1 from LPS-primed cells in vivo. J. Immunol. 154, 2821-2828 (1995).
48. Perregaux, D. G., McNiff, P., Laliberte, R., Conklyn, M. & Gabel, C. A. ATP acts as an agonist to promote stimulus-induced secretion of IL-1 beta and IL-18 in human blood. J. Immunol. 165, 4615-4623 (2000).
49. Li, W., Li, J., Sama, A. E. & Wang, H. Carbenoxolone Blocks Endotoxin-Induced Protein Kinase R (PKR) Activation and High Mobility Group Box 1 (HMGB1) Release. Mol. Med. 19, 203-211 (2013).
50. Surprenant, A., Rassendren, F., Kawashima, E., North, R. A. & Buell, G. The cytolytic P2Z receptor for extracellular ATP identified as a P2X receptor (P2X7). Science. 272, 735-738 (1996).
51. Kang, J. et al. Connexin 43 hemichannels are permeable to ATP. J. Neurosci. 28, 4702-4711 (2008).
52. Beyer, E. C. & Steinberg, T. H. Evidence that the gap junction protein connexin-43 is the ATP-induced pore of mouse macrophages. J. Biol. Chem. 266, 7971-7974 (1991).
53. Chekeni, F. B. et al. Pannexin 1 channels mediate 'find-me' signal release and membrane permeability during apoptosis. Nature. 467, 863-867 (2010).
54. Qu, Y. et al. Pannexin-1 is required for ATP release during apoptosis but not for inflammasome activation. J. Immunol. 186, 6553-6561 (2011).
55. Pelegrin, P. & Surprenant, A. Pannexin-1 mediates large pore formation and interleukin-1beta release by the ATP-gated P2X7 receptor. EMBO J. 25, 5071-5082 (2006).
56. Locovei, S., Scemes, E., Qiu, F., Spray, D. C. & Dahl, G. Pannexin1 is part of the pore forming unit of the P2X(7) receptor death complex. FEBS Lett. 581, 483-488 (2007).
57. Baroja-Mazo, A., Barbera-Cremades, M. & Pelegrin, P. The participation of plasma membrane hemichannels to purinergic signaling. Biochim. Biophys. Acta. 1828, 79-93 (2013).
58. Di Virgilio, F. Liaisons dangereuses: P2X(7) and the inflammasome. Trends Pharmacol. Sci. 28, 465-472 (2007).
59. Humphreys, B. D. & Dubyak, G. R. Induction of the P2z/P2X7 nucleotide receptor and associated phospholipase D activity by lipopolysaccharide and IFN-gamma in the human THP-1 monocytic cell line. J. Immunol. 157, 5627-5637 (1996).
60. Ferrari, D., Chiozzi, P., Falzoni, S., Hanau, S. & Di Virgilio, F. Purinergic modulation of interleukin-1 beta release from microglial cells stimulated with bacterial endotoxin. J. Exp. Med. 185, 579-582 (1997).
61. Okamoto, T. & Kanda, T. Glycyrrhizin protects mice from concanavalin A-induced hepatitis without affecting cytokine expression. Int. J. Mol. Med. 4, 149-152 (1999).
62. Mabuchi, A., Wake, K., Marlini, M., Watanabe, H. & Wheatley, A. M. Protection by glycyrrhizin against warm ischemia-reperfusion-induced cellular injury and derangement of the microcirculatory blood flow in the rat liver. Microcirculation. 16, 364-376 (2009).
63. Ogiku, M., Kono, H., Hara, M., Tsuchiya, M. & Fujii, H. Glycyrrhizin prevents liver injury by inhibition of high-mobility group box 1 production by Kupffer cells after ischemia-reperfusion in rats. J. Pharmacol. Exp. Ther. 339, 93-98 (2011).
64. Kuroda, N. et al. Apoptotic response through a high mobility box 1 protein-dependent mechanism in LPS/GalN-induced mouse liver failure and glycyrrhizin-mediated inhibition. PLoS. One. 9, e92884 (2014).
65. Wang, X., Sun, R., Wei, H. & Tian, Z. High-mobility group box 1 (HMGB1)-Toll-like receptor (TLR)4-interleukin (IL)-23-IL-17A axis in drug-induced damage-associated lethal hepatitis: Interaction of gammadelta T cells with macrophages. Hepatology. 57, 373-384 (2013).
66. Yoshida, T. et al. Inhibitory effect of glycyrrhizin on lipopolysaccharide and d-galactosamine-induced mouse liver injury. Eur. J. Pharmacol. 576, 136-142 (2007).
67. Wang, W. et al. Glycyrrhizin protects against porcine endotoxemia through modulation of systemic inflammatory response. Crit Care. 17, R44 (2013).
68. Liu, Y. et al. Protective effects of glycyrrhizic acid by rectal treatment on a TNBS-induced rat colitis model. J. Pharm. Pharmacol. 63, 439-446 (2011).

69. Shearman, D. J. & Hetzel, D. The medical management of peptic ulcer. Annu. Rev. Med. 30:61-79, 61-79 (1979).
70. Ma, W., Hui, H., Pelegrin, P. & Surprenant, A. Pharmacological characterization of pannexin-1 currents expressed in mammalian cells. J. Pharmacol. Exp. Ther. 328, 409-418 (2009).
71. Poornima, V. et al. P2X7 receptor-pannexin 1 hemichannel association: effect of extracellular calcium on membrane permeabilization. J. Mol. Neurosci. 46, 585-594 (2012).
72. Thompson, R. J., Zhou, N. & MacVicar, B. A. Ischemia opens neuronal gap junction hemichannels. Science. 312, 924-927 (2006).
73. Reigada, D., Lu, W., Zhang, M. & Mitchell, C. H. Elevated pressure triggers a physiological release of ATP from the retina: Possible role for pannexin hemichannels. Neuroscience. %19; 157, 396-404 (2008).
74. Sridharan, M. et al. Pannexin 1 is the conduit for low oxygen tension-induced ATP release from human erythrocytes. Am. J. Physiol Heart Circ. Physiol. 299, H1146-H1152 (2010).
75. Pelegrin, P. & Surprenant, A. Dynamics of macrophage polarization reveal new mechanism to inhibit IL-1beta release through pyrophosphates. EMBO J. 28, 2114-2127 (2009).
76. Suzuki, S. et al. Effects of carbenoxolone on alveolar fluid clearance and lung inflammation in the rat. Crit Care Med. 32, 1910-1915 (2004).
77. Tamura, K., Alessandri, B., Heimann, A. & Kempski, O. The effect of a gap junction blocker, carbenoxolone, on ischemic brain injury and cortical spreading depression. Neuroscience. 194:262-71. Epub; %2011 Aug. 3, 262-271 (2011).
78. Li, W. et al. A cardiovascular drug rescues mice from lethal sepsis by selectively attenuating a late-acting proinflammatory mediator, high mobility group box 1. J. Immunol. 178, 3856-3864 (2007).
79. Chen, G. et al. Bacterial endotoxin stimulates macrophages to release HMGB1 partly through CD14- and TNF-dependent mechanisms. J Leukoc. Biol 76, 994-1001 (2004).
80. Li, W. et al. Characterization of human SAA, but not SAA1, as a positive regulator of HMGB1 release. Shock 41(Suppl 2), 46-47. 6-February 2014.
81. Eugenin, E. A. Role of connexin/pannexin containing channels in infectious diseases. FEBS Lett. 588, 1389-1395 (2014).
82. Fernandez-Cobo, M., Gingalewski, C. & De Maio, A. Expression of the connexin 43 gene is increased in the kidneys and the lungs of rats injected with bacterial lipopolysaccharide. Shock. 10, 97-102 (1998).
83. Jara, P. I., Boric, M. P. & Saez, J. C. Leukocytes express connexin 43 after activation with lipopolysaccharide and appear to form gap junctions with endothelial cells after ischemia-reperfusion. Proc. Natl. Acad. Sci. U.S.A. 92, 7011-7015 (1995).
84. Eugenin, E. A., Branes, M. C., Berman, J. W. & Saez, J. C. TNF-alpha plus IFN-gamma induce connexin43 expression and formation of gap junctions between human monocytes/macrophages that enhance physiological responses. J. Immunol. 170, 1320-1328 (2003).
85. Sirois, C. M. et al. RAGE is a nucleic acid receptor that promotes inflammatory responses to DNA. J. Exp. Med. 210, 2447-2463 (2013).
86. Kokkola, R. et al. RAGE is the Major Receptor for the Proinflammatory Activity of HMGB1 in Rodent Macrophages. Scand. J Immunol 61, 1-9 (2005).
87. Cai, H. et al. Serum amyloid A induces monocyte tissue factor. J. Immunol. 178, 1852-1860 (2007).
88. Aliprantis, A. O. et al. Cell activation and apoptosis by bacterial lipoproteins through toll-like receptor-2. Science. 285, 736-739 (1999).
89. Cheng, N., He, R., Tian, J., Ye, P. P. & Ye, R. D. Cutting edge: TLR2 is a functional receptor for acute-phase serum amyloid A. J. Immunol. 181, 22-26 (2008).
90. Chen, E. S. et al. Serum amyloid A regulates granulomatous inflammation in sarcoidosis through Toll-like receptor-2. Am. J. Respir. Crit Care Med. 181, 360-373 (2010).
91. Sandri, S. et al. Is serum amyloid A an endogenous TLR4 agonist? J. Leukoc. Biol. 83, 1174-1180 (2008).
92. Beutler, B. Tlr4: central component of the sole mammalian LPS sensor. Curr. Opin. Immunol 12, 20-26 (2000).
93. Yu, M. et al. HMGB1 signals through toll-like receptor (TLR) 4 and TLR2. Shock. 26, 174-179 (2006).
94. Li, W. et al. A hepatic protein, fetuin-A, occupies a protective role in lethal systemic inflammation. PLoS ONE 6, e16945 (2011).
95. Li, W. et al. EGCG stimulates autophagy and reduces cytoplasmic HMGB1 levels in endotoxin-stimulated macrophages. Biochem. Pharmacol. 81, 1152-1163 (2011).
96. Lohman, A. W. & Isakson, B. E. Differentiating connexin hemichannels and pannexin channels in cellular ATP release. FEBS Lett. 588, 1379-1388 (2014).
97. Thompson, R. J. et al. Activation of pannexin-1 hemichannels augments aberrant bursting in the hippocampus. Science. 322, 1555-1559 (2008).
98. Stridh, M. H. et al. Enhanced glutathione efflux from astrocytes in culture by low extracellular Ca2+ and curcumin. Neurochem. Res. 35, 1231-1238 (2010).
99. Silverman, W., Locovei, S. & Dahl, G. Probenecid, a gout remedy, inhibits pannexin 1 channels. Am. J. Physiol Cell Physiol. 295, C761-C767 (2008).
100. Wang, N. et al. Selective inhibition of Cx43 hemichannels by Gap19 and its impact on myocardial ischemia/reperfusion injury. Basic Res. Cardiol. 108, 309-0309 (2013).
101. Yanai, H. et al. Conditional ablation of HMGB1 in mice reveals its protective function against endotoxemia and bacterial infection. Proc. Natl. Acad. Sci. U.S.A. 110, 20699-20704 (2013).
102. Huang, H. et al. Hepatocyte-specific high-mobility group box 1 deletion worsens the injury in liver ischemia/reperfusion: a role for intracellular high-mobility group box 1 in cellular protection. Hepatology. 59, 1984-1997 (2014).
103. Kang, R. et al. Intracellular Hmgb1 inhibits inflammatory nucleosome release and limits acute pancreatitis in mice. Gastroenterology. 146, 1097-1107 (2014).
104. Kang, R. et al. HMGB1 in health and disease. Mol. Aspects Med. 10 (2014).
105. Westphalen, K. et al. Sessile alveolar macrophages communicate with alveolar epithelium to modulate immunity. Nature. 506, 503-506 (2014).
106. Sarieddine, M. Z. et al. Connexin43 modulates neutrophil recruitment to the lung. J. Cell Mol. Med. 13, 4560-4570 (2009).
107. Cronin, M., Anderson, P. N., Cook, J. E., Green, C. R. & Becker, D. L. Blocking connexin43 expression reduces inflammation and improves functional recovery after spinal cord injury. Mol. Cell Neurosci. 39, 152-160 (2008).

108. Abed, A. et al. Targeting connexin 43 protects against the progression of experimental chronic kidney disease in mice. Kidney Int. 10 (2014).
109. Tsuchida, S. et al. Silencing the expression of connexin 43 decreases inflammation and joint destruction in experimental arthritis. J. Orthop. Res. 31, 525-530 (2013).
110. Sakamoto, R., Okano, M., Takena, H. & Ohtsuki, K. Inhibitory effect of glycyrrhizin on the phosphorylation and DNA-binding abilities of high mobility group proteins 1 and 2 in vitro. Biol. Pharm. Bull. 24, 906-911 (2001).
111. Mollica, L. et al. Glycyrrhizin binds to high-mobility group box 1 protein and inhibits its cytokine activities. Chem. Biol. 14, 431-441 (2007).
112. Yamaguchi, H., Kidachi, Y., Kamiie, K., Noshita, T. & Umetsu, H. Structural insight into the ligand-receptor interaction between glycyrrhetinic acid (GA) and the high-mobility group protein B1 (HMGB1)-DNA complex. Bioinformation. 8, 1147-1153 (2012).
113. Kim, S. W. et al. Glycyrrhizic acid affords robust neuroprotection in the postischemic brain via anti-inflammatory effect by inhibiting HMGB1 phosphorylation and secretion. Neurobiol. Dis. 46, 147-156 (2012).
114. Luo, L., Jin, Y., Kim, I. D. & Lee, J. K. Glycyrrhizin Suppresses HMGB1 Inductions in the Hippocampus and Subsequent Accumulation in Serum of a Kainic Acid-Induced Seizure Mouse Model. Cell Mol. Neurobiol. 34, 987-997 (2014).
115. Musumeci, D., Roviello, G. N. & Montesarchio, D. An overview on HMGB1 inhibitors as potential therapeutic agents in HMGB1-related pathologies. Pharmacol. Ther. 141, 347-357 (2014).
116. Ohnishi, M. et al. HMGB1 inhibitor glycyrrhizin attenuates intracerebral hemorrhage-induced injury in rats. Neuropharmacology. 61, 975-980 (2011).
117. Yang, H. et al. MD-2 is required for disulfide HMGB1-dependent TLR4 signaling GOOGLE. J. Exp. Med. in press. 2014.
118. Yang, H. et al. A critical cysteine is required for HMGB1 binding to Toll-like receptor 4 and activation of macrophage cytokine release. Proc. Natl. Acad. Sci. U.S.A. 107, 11942-11947 (2010).

What is claimed is:

1. A method of treating ischemia-reperfusion injury in a subject or of reducing or inhibiting development of ischemia-reperfusion injury in a subject, the method comprising administering to the subject an amount of a peptide consisting of ENVCYD (SEQ ID NO:1) sufficient to treat ischemia-reperfusion injury, or sufficient to reduce or inhibit development of ischemia-reperfusion injury.

2. The method of claim 1, wherein the subject already has ischemia-reperfusion injury and the method is to treat ischemia-reperfusion injury in the subject.

3. The method of claim 1, wherein the method is to reduce or inhibit ischemia-reperfusion injury in the subject.

4. The method of claim 1, wherein carbenoxolone, glycyrrhizic acid, glycyrrhitinic acid, or monoammonium glycyrrhizinate is also administered to the subject.

* * * * *

SEQUENCE LISTING

```
<160> NUMBER OF SEQ ID NOS: 19

<210> SEQ ID NO 1
<211> LENGTH: 6
<212> TYPE: PRT
<213> ORGANISM: Homo Sapiens

<400> SEQUENCE: 1

Glu Asn Val Cys Tyr Asp
1               5

<210> SEQ ID NO 2
<211> LENGTH: 6
<212> TYPE: PRT
<213> ORGANISM: Homo Sapiens

<400> SEQUENCE: 2

Asn Val Cys Tyr Asp Lys
1               5

<210> SEQ ID NO 3
<211> LENGTH: 6
<212> TYPE: PRT
<213> ORGANISM: Homo Sapiens

<400> SEQUENCE: 3

Ala Phe Arg Cys Asn Thr
1               5

<210> SEQ ID NO 4
<211> LENGTH: 6
<212> TYPE: PRT
<213> ORGANISM: Homo Sapiens

<400> SEQUENCE: 4

Phe Arg Cys Asn Thr Gln
1               5

<210> SEQ ID NO 5
<211> LENGTH: 6
<212> TYPE: PRT
<213> ORGANISM: Homo Sapiens
```

```
<400> SEQUENCE: 5

Gln Pro Gly Cys Glu Asn
1               5

<210> SEQ ID NO 6
<211> LENGTH: 6
<212> TYPE: PRT
<213> ORGANISM: Homo Sapiens

<400> SEQUENCE: 6

Pro Gly Cys Glu Asn Val
1               5

<210> SEQ ID NO 7
<211> LENGTH: 6
<212> TYPE: PRT
<213> ORGANISM: Homo Sapiens

<400> SEQUENCE: 7

Val Cys Tyr Asp Lys Ser
1               5

<210> SEQ ID NO 8
<211> LENGTH: 6
<212> TYPE: PRT
<213> ORGANISM: Homo Sapiens

<400> SEQUENCE: 8

Tyr Asp Lys Ser Phe Pro
1               5

<210> SEQ ID NO 9
<211> LENGTH: 5
<212> TYPE: PRT
<213> ORGANISM: Homo Sapiens

<400> SEQUENCE: 9

Phe Pro Ile Ser His
1               5

<210> SEQ ID NO 10
<211> LENGTH: 5
<212> TYPE: PRT
<213> ORGANISM: Homo Sapiens

<400> SEQUENCE: 10

Ile Ser His Val Arg
1               5

<210> SEQ ID NO 11
<211> LENGTH: 382
<212> TYPE: PRT
<213> ORGANISM: Homo Sapiens

<400> SEQUENCE: 11

Met Gly Asp Trp Ser Ala Leu Gly Lys Leu Leu Asp Lys Val Gln Ala
1               5                   10                  15

Tyr Ser Thr Ala Gly Gly Lys Val Trp Leu Ser Val Leu Phe Ile Phe
                20                  25                  30

Arg Ile Leu Leu Leu Gly Thr Ala Val Glu Ser Ala Trp Gly Asp Glu
            35                  40                  45

Gln Ser Ala Phe Arg Cys Asn Thr Gln Gln Pro Gly Cys Glu Asn Val
        50                  55                  60
```

Cys Tyr Asp Lys Ser Phe Pro Ile Ser His Val Arg Phe Trp Val Leu
 65                  70                  75                  80

Gln Ile Ile Phe Val Ser Val Pro Thr Leu Leu Tyr Leu Ala His Val
                 85                  90                  95

Phe Tyr Val Met Arg Lys Glu Glu Lys Leu Asn Lys Lys Glu Glu Glu
            100                 105                 110

Leu Lys Val Ala Gln Thr Asp Gly Val Asn Val Asp Met His Leu Lys
        115                 120                 125

Gln Ile Glu Ile Lys Lys Phe Lys Tyr Gly Ile Glu Glu His Gly Lys
    130                 135                 140

Val Lys Met Arg Gly Gly Leu Leu Arg Thr Tyr Ile Ile Ser Ile Leu
145                 150                 155                 160

Phe Lys Ser Ile Phe Glu Val Ala Phe Leu Leu Ile Gln Trp Tyr Ile
                165                 170                 175

Tyr Gly Phe Ser Leu Ser Ala Val Tyr Thr Cys Lys Arg Asp Pro Cys
            180                 185                 190

Pro His Gln Val Asp Cys Phe Leu Ser Arg Pro Thr Glu Lys Thr Ile
        195                 200                 205

Phe Ile Ile Phe Met Leu Val Val Ser Leu Val Ser Leu Ala Leu Asn
    210                 215                 220

Ile Ile Glu Leu Phe Tyr Val Phe Phe Lys Gly Val Lys Asp Arg Val
225                 230                 235                 240

Lys Gly Lys Ser Asp Pro Tyr His Ala Thr Ser Gly Ala Leu Ser Pro
                245                 250                 255

Ala Lys Asp Cys Gly Ser Gln Lys Tyr Ala Tyr Phe Asn Gly Cys Ser
            260                 265                 270

Ser Pro Thr Ala Pro Leu Ser Pro Met Ser Pro Gly Tyr Lys Leu
        275                 280                 285

Val Thr Gly Asp Arg Asn Asn Ser Ser Cys Arg Asn Tyr Asn Lys Gln
    290                 295                 300

Ala Ser Glu Gln Asn Trp Ala Asn Tyr Ser Ala Glu Gln Asn Arg Met
305                 310                 315                 320

Gly Gln Ala Gly Ser Thr Ile Ser Asn Ser His Ala Gln Pro Phe Asp
                325                 330                 335

Phe Pro Asp Asp Asn Gln Asn Ser Lys Lys Leu Ala Ala Gly His Glu
            340                 345                 350

Leu Gln Pro Leu Ala Ile Val Asp Gln Arg Pro Ser Ser Arg Ala Ser
        355                 360                 365

Ser Arg Ala Ser Ser Arg Pro Arg Pro Asp Asp Leu Glu Ile
    370                 375                 380

<210> SEQ ID NO 12
<211> LENGTH: 36
<212> TYPE: PRT
<213> ORGANISM: Homo Sapiens

<400> SEQUENCE: 12

Ser Ala Trp Gly Asp Glu Gln Ser Ala Phe Arg Cys Asn Thr Gln Gln
1               5                   10                  15

Pro Gly Cys Glu Asn Val Cys Tyr Cys Tyr Asp Lys Ser Phe Pro Ile
            20                  25                  30

Ser His Val Arg
        35

<210> SEQ ID NO 13
<211> LENGTH: 15
<212> TYPE: PRT
<213> ORGANISM: Homo Sapiens

<400> SEQUENCE: 13

Val Cys Tyr Cys Tyr Asp Lys Ser Phe Pro Ile Ser His Val Arg
1               5                   10                  15

<210> SEQ ID NO 14
<211> LENGTH: 6
<212> TYPE: PRT
<213> ORGANISM: HOMO SAPIENS

<400> SEQUENCE: 14

Glu Asn Val Ser Tyr Asp
1               5

<210> SEQ ID NO 15
<211> LENGTH: 382
<212> TYPE: PRT
<213> ORGANISM: HOMO SAPIENS

<400> SEQUENCE: 15

Met Gly Asp Trp Ser Ala Leu Gly Lys Leu Leu Asp Lys Val Gln Ala
1               5                   10                  15

Tyr Ser Thr Ala Gly Gly Lys Val Trp Leu Ser Val Leu Phe Ile Phe
                20                  25                  30

Arg Ile Leu Leu Leu Gly Thr Ala Val Glu Ser Ala Trp Gly Asp Glu
            35                  40                  45

Gln Ser Ala Phe Arg Cys Asn Thr Gln Gln Pro Gly Cys Glu Asn Val
        50                  55                  60

Cys Tyr Asp Lys Ser Phe Pro Ile Ser His Val Arg Phe Trp Val Leu
65                  70                  75                  80

Gln Ile Ile Phe Val Ser Val Pro Thr Leu Leu Tyr Leu Ala His Val
                85                  90                  95

Phe Tyr Val Met Arg Lys Glu Glu Lys Leu Asn Lys Lys Glu Glu Glu
                100                 105                 110

Leu Lys Val Ala Gln Thr Asp Gly Val Asn Val Asp Met His Leu Lys
            115                 120                 125

Gln Ile Glu Ile Lys Lys Phe Lys Tyr Gly Ile Glu Glu His Gly Lys
        130                 135                 140

Val Lys Met Arg Gly Gly Leu Leu Arg Thr Tyr Ile Ile Ser Ile Leu
145                 150                 155                 160

Phe Lys Ser Ile Phe Glu Val Ala Phe Leu Leu Ile Gln Trp Tyr Ile
                165                 170                 175

Tyr Gly Phe Ser Leu Ser Ala Val Tyr Thr Cys Lys Arg Asp Pro Cys
                180                 185                 190

Pro His Gln Val Asp Cys Phe Leu Ser Arg Pro Thr Glu Lys Thr Ile
            195                 200                 205

Phe Ile Ile Phe Met Leu Val Val Ser Leu Val Ser Leu Ala Leu Asn
        210                 215                 220

Ile Ile Glu Leu Phe Tyr Val Phe Phe Lys Gly Val Lys Asp Arg Val
225                 230                 235                 240

Lys Gly Lys Ser Asp Pro Tyr His Ala Thr Ser Gly Ala Leu Ser Pro
                245                 250                 255

Ala Lys Asp Cys Gly Ser Gln Lys Tyr Ala Tyr Phe Asn Gly Cys Ser
                260                 265                 270

```
Ser Pro Thr Ala Pro Leu Ser Pro Met Ser Pro Pro Gly Tyr Lys Leu
        275                 280                 285

Val Thr Gly Asp Arg Asn Asn Ser Ser Cys Arg Asn Tyr Asn Lys Gln
290                 295                 300

Ala Ser Glu Gln Asn Trp Ala Asn Tyr Ser Ala Glu Gln Asn Arg Met
305                 310                 315                 320

Gly Gln Ala Gly Ser Thr Ile Ser Asn Ser His Ala Gln Pro Phe Asp
                325                 330                 335

Phe Pro Asp Asp Asn Gln Asn Ser Lys Lys Leu Ala Ala Gly His Glu
                340                 345                 350

Leu Gln Pro Leu Ala Ile Val Asp Gln Arg Pro Ser Ser Arg Ala Ser
                355                 360                 365

Ser Arg Ala Ser Ser Arg Pro Arg Pro Asp Asp Leu Glu Ile
        370                 375                 380

<210> SEQ ID NO 16
<211> LENGTH: 426
<212> TYPE: PRT
<213> ORGANISM: HOMO SAPIENS

<400> SEQUENCE: 16

Met Ala Ile Ala Gln Leu Ala Thr Glu Tyr Val Phe Ser Asp Phe Leu
1               5                   10                  15

Leu Lys Glu Pro Thr Glu Pro Lys Phe Lys Gly Leu Arg Leu Glu Leu
                20                  25                  30

Ala Val Asp Lys Met Val Thr Cys Ile Ala Val Gly Leu Pro Leu Leu
            35                  40                  45

Leu Ile Ser Leu Ala Phe Ala Gln Glu Ile Ser Ile Gly Thr Gln Ile
        50                  55                  60

Ser Cys Phe Ser Pro Ser Ser Phe Ser Trp Arg Gln Ala Ala Phe Val
65                  70                  75                  80

Asp Ser Tyr Cys Trp Ala Ala Val Gln Gln Lys Asn Ser Leu Gln Ser
                85                  90                  95

Glu Ser Gly Asn Leu Pro Leu Trp Leu His Lys Phe Phe Pro Tyr Ile
                100                 105                 110

Leu Leu Leu Phe Ala Ile Leu Leu Tyr Leu Pro Pro Leu Phe Trp Arg
            115                 120                 125

Phe Ala Ala Ala Pro His Ile Cys Ser Asp Leu Lys Phe Ile Met Glu
        130                 135                 140

Glu Leu Asp Lys Val Tyr Asn Arg Ala Ile Lys Ala Ala Lys Ser Ala
145                 150                 155                 160

Arg Asp Leu Asp Met Arg Asp Gly Ala Cys Ser Val Pro Gly Val Thr
                165                 170                 175

Glu Asn Leu Gly Gln Ser Leu Trp Glu Val Ser Glu Ser His Phe Lys
                180                 185                 190

Tyr Pro Ile Val Glu Gln Tyr Leu Lys Thr Lys Lys Asn Ser Asn Asn
            195                 200                 205

Leu Ile Ile Lys Tyr Ile Ser Cys Arg Leu Leu Thr Leu Ile Ile Ile
        210                 215                 220

Leu Leu Ala Cys Ile Tyr Leu Gly Tyr Tyr Phe Ser Leu Ser Ser Leu
225                 230                 235                 240

Ser Asp Glu Phe Val Cys Ser Ile Lys Ser Gly Ile Leu Arg Asn Asp
                245                 250                 255

Ser Thr Val Pro Asp Gln Phe Gln Cys Lys Leu Ile Ala Val Gly Ile
```

-continued

```
                260                 265                 270
Phe Gln Leu Leu Ser Val Ile Asn Leu Val Tyr Val Leu Leu Ala
            275                 280                 285

Pro Val Val Tyr Thr Leu Phe Val Pro Phe Arg Gln Lys Thr Asp
        290                 295                 300

Val Leu Lys Val Tyr Glu Ile Leu Pro Thr Phe Asp Val Leu His Phe
305                 310                 315                 320

Lys Ser Glu Gly Tyr Asn Asp Leu Ser Leu Tyr Asn Leu Phe Leu Glu
                325                 330                 335

Glu Asn Ile Ser Glu Val Lys Ser Tyr Lys Cys Leu Lys Val Leu Glu
            340                 345                 350

Asn Ile Lys Ser Ser Gly Gln Gly Ile Asp Pro Met Leu Leu Leu Thr
            355                 360                 365

Asn Leu Gly Met Ile Lys Met Asp Val Val Asp Gly Lys Thr Pro Met
        370                 375                 380

Ser Ala Glu Met Arg Glu Glu Gln Gly Asn Gln Thr Ala Glu Leu Gln
385                 390                 395                 400

Gly Met Asn Ile Asp Ser Glu Thr Lys Ala Asn Asn Gly Glu Lys Asn
                405                 410                 415

Ala Arg Gln Arg Leu Leu Asp Ser Ser Cys
            420                 425

<210> SEQ ID NO 17
<211> LENGTH: 13
<212> TYPE: PRT
<213> ORGANISM: HOMO SAPIENS

<400> SEQUENCE: 17

Val Cys Tyr Asp Lys Ser Phe Pro Ile Ser His Val Arg
1               5                   10

<210> SEQ ID NO 18
<211> LENGTH: 11
<212> TYPE: PRT
<213> ORGANISM: HOMO SAPIENS

<400> SEQUENCE: 18

Ser Arg Pro Thr Glu Lys Thr Ile Phe Ile Ile
1               5                   10

<210> SEQ ID NO 19
<211> LENGTH: 9
<212> TYPE: PRT
<213> ORGANISM: HOMO SAPIENS

<400> SEQUENCE: 19

Lys Gln Ile Glu Ile Lys Lys Phe Lys
1               5
```